US010022157B2

(12) United States Patent
Walker et al.

(10) Patent No.: US 10,022,157 B2
(45) Date of Patent: *Jul. 17, 2018

(54) CONVERTIBLE SCREW FOR SPINAL FIXATION

(71) Applicant: BLACKSTONE MEDICAL, INC., Lewisvile, TX (US)

(72) Inventors: Clinton Walker, Frisco, TX (US); Bryan Jones, Little Elm, TX (US)

(73) Assignee: Blackstone Medical, Inc., Lewisville, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/947,075

(22) Filed: Nov. 20, 2015

(65) Prior Publication Data

US 2017/0143379 A1    May 25, 2017

(51) Int. Cl.
*A61B 17/88* (2006.01)
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/7055* (2013.01); *A61B 17/8685* (2013.01)

(58) Field of Classification Search
CPC ............ A61B 17/7037; A61B 17/7032; A61B 17/7055; A61B 17/8685
USPC ........ 606/266, 267, 268, 269, 270, 272, 279
See application file for complete search history.

(56) References Cited

U.S. PATENT DOCUMENTS

| 5,728,046 | A | 3/1998 | Mayer et al. |
| 6,964,666 | B2 | 11/2005 | Jackson |
| 7,651,502 | B2 | 1/2010 | Jackson |
| 7,887,539 | B2 | 2/2011 | Dunbar, Jr. et al. |
| 7,887,541 | B2 | 2/2011 | Runco et al. |
| 7,918,858 | B2 | 4/2011 | Stad et al. |
| 8,100,951 | B2 | 1/2012 | Justis et al. |
| 8,172,847 | B2 | 5/2012 | Dziedzic et al. |
| 8,303,595 | B2 | 11/2012 | Jones |
| 8,308,728 | B2 | 11/2012 | Lott et al. |
| 8,357,184 | B2 | 1/2013 | Woolley et al. |
| 8,435,269 | B2 | 5/2013 | Woolley et al. |
| 8,500,750 | B2 | 8/2013 | Varieur et al. |
| 8,535,320 | B2 | 9/2013 | Woolley et al. |
| 8,545,505 | B2 | 10/2013 | Sandstrom et al. |
| 8,556,903 | B2 | 10/2013 | Miller et al. |
| 8,603,145 | B2 | 12/2013 | Forton et al. |

(Continued)

*Primary Examiner* — Pedro Philogene
*Assistant Examiner* — David C Comstock
(74) *Attorney, Agent, or Firm* — Baker & McKenzie LLP

(57) ABSTRACT

Disclosed herein are spinal fixation systems that may comprise a screw, a body, and a pressure cap. A screw may comprise a head at a proximal end, a bone connection element at a distal end, and a first mating element disposed on a head of a pedicle screw. A body may comprise a proximal end, a distal end, a mounting rod receiving channel at a proximal end, and a screw head receiving aperture at a distal end. A portion of the mounting rod receiving channel may be operable to receive a compression element. A pressure cap may comprise a proximal end, distal end, and a second mating element on a distal end. A first mating element of the screw may be configured to mate with the second mating element of the pressure cap thereby limiting the pivotal movement of the screw to that of a monoaxial screw.

13 Claims, 13 Drawing Sheets

(56) References Cited

U.S. PATENT DOCUMENTS

| | | | |
|---|---|---|---|
| 8,608,746 B2 | 12/2013 | Kolb et al. | |
| 9,358,047 B2* | 6/2016 | Mishra | A61B 17/7037 |
| 9,480,501 B2* | 11/2016 | Fang | A61B 17/7037 |
| 2003/0149341 A1 | 8/2003 | Clifton | |
| 2004/0230191 A1 | 11/2004 | Frey et al. | |
| 2004/0267275 A1 | 12/2004 | Cournoyer et al. | |
| 2006/0025771 A1* | 2/2006 | Jackson | A61B 17/7032 74/1 R |
| 2008/0119849 A1* | 5/2008 | Beardsley | A61B 17/7032 606/306 |
| 2009/0198280 A1* | 8/2009 | Spratt | A61B 17/7037 606/267 |
| 2010/0152785 A1 | 6/2010 | Forton et al. | |
| 2011/0046684 A1* | 2/2011 | Abdelgany | A61B 17/7037 606/305 |
| 2012/0221055 A1* | 8/2012 | Copf | A61B 17/7041 606/264 |
| 2015/0112390 A1* | 4/2015 | Fang | A61B 17/7037 606/266 |
| 2017/0049482 A1* | 2/2017 | Campbell | A61B 17/866 |

\* cited by examiner

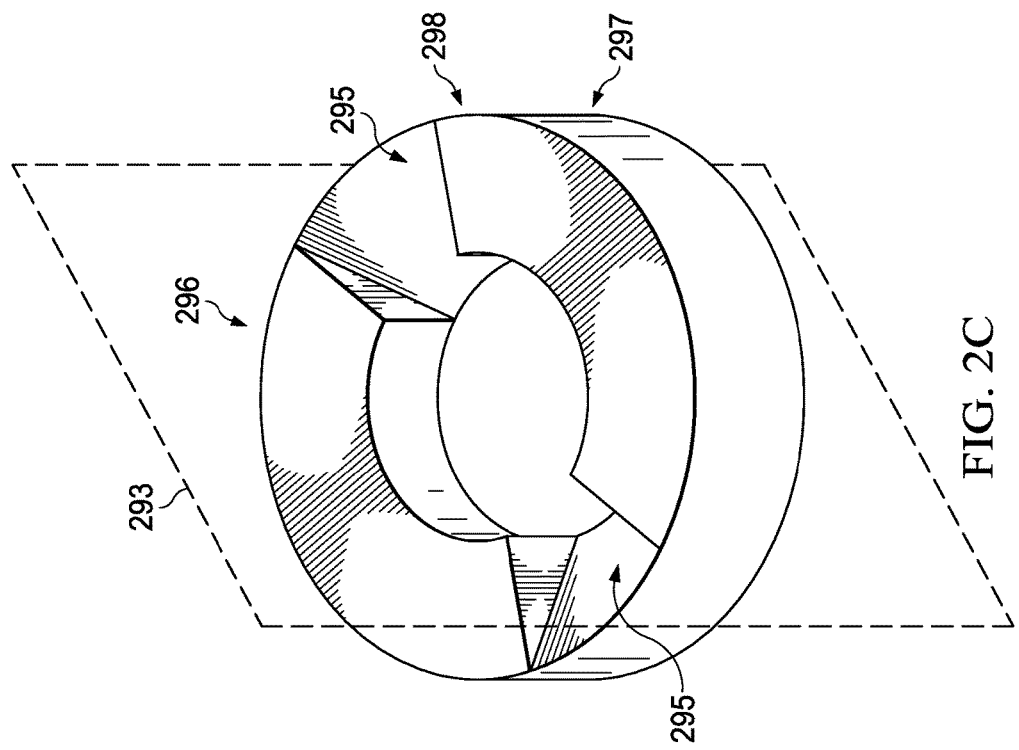
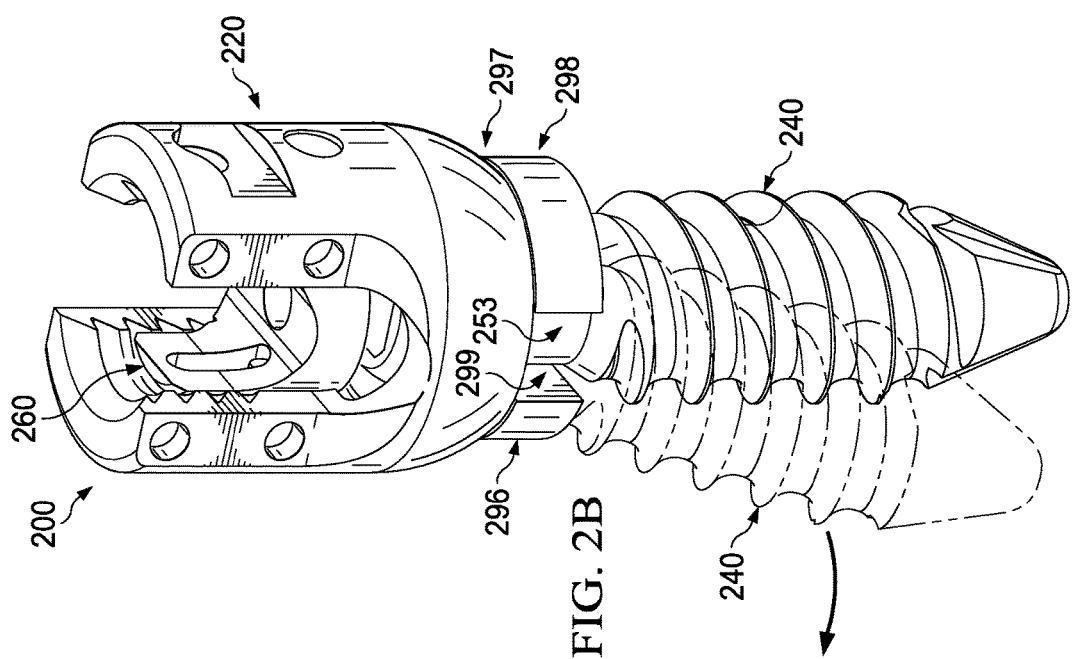

US 10,022,157 B2

CONVERTIBLE SCREW FOR SPINAL FIXATION

FIELD OF THE DISCLOSURE

The present disclosure relates, in some embodiments, to screws for spinal fixation applications, and more specifically, in some embodiments, to convertible pedicle screws for use in spinal fixation systems.

BACKGROUND OF THE DISCLOSURE

Various systems exist for connecting fastener elements (e.g., pedicle screws, iliac screws, cervical screws) to bones for the purpose of spinal (e.g., vertebral, iliac, cervical) fixation. Such systems may use a plurality of screws fitted in bodies, wherein a plurality of bodies are aligned using a mounting rod.

A spinal fixation system may comprise several components with various degrees of stability or various degrees of movement between the components themselves or between the components and the bones to which they are affixed. For example, the connection between the bones and the fastener may have a degree of stability. Greater stability may help promote a more secure system and a more secure fixation for multiple segments of the spine. However, overly rigid or inflexibly positioned fastener elements may prevent the mounting rod from being aligned properly along a plurality of spinal elements (e.g., vertebrae).

For surgical proceedings, the components intended to be used for the spinal fixation system may often be preselected. Such selection may be made based on a number of factors such as the particular dimensions of the components and the anatomical location for the fixation of the system. However, sometimes during the actual surgery, the preselected components may be determined to not actually be ideal. This may be the case when the preselected components allow for too much or not enough movement or flexibility of the fastener elements.

SUMMARY

Accordingly, a need has arisen for improved spinal fixation systems that promote secure and stable connections, allow for a desired degree of movement for the fastener elements, and may allow for on-the-spot adjustment or conversion of components during surgical procedures. Explained further, it may be desirable to restrict the movement of a fastener element that initially allowed for a more expansive degree of movement. For example, it may be desirable for a fastener element to initially be capable of polyaxial movement to promote ideal alignment of the mounting rod, followed by restriction of the fastener element to monoaxial movement to provide a more stable connection.

The present disclosure relates, according to some embodiments, to a spinal fixation system that may comprise a mounting rod, a screw, a body, and a pressure cap. A screw may comprise a screw head at a proximal end, a bone connection element at a distal end; and a first mating element disposed on the screw head, according to some embodiments. In some embodiments, the head of the screw comprises a substantially spherical surface. According to some embodiments the bone connection element of the screw comprises an external thread operable to be secured into a portion of a spine. The bone connection element may have a diameter of about 2.5 mm to about 12 mm. The bone connection element may have a length of about 6 mm to about 120 mm.

A body may comprise a proximal end, a distal end, a mounting rod receiving channel disposed at the proximal end, and a screw head receiving aperture disposed at the distal end. A proximal end and a distal end may be disposed along a longitudinal axis of the body. The mounting rod receiving channel may be configured to receive a mounting rod. In some embodiments, a mounting rod receiving channel may comprise an internal thread for receiving a compression element. The mounting rod receiving channel may be operable to receive a mounting rod at an angle substantially orthogonal to the longitudinal axis of the body. In some embodiments the body may be frangibly connected to an attachment portion to form a tower.

In some embodiments, the spinal fixation system may include a compression element disposed at the proximal portion of the mounting rod receiving channel. The compression element may be operable to apply a bias to a proximal surface of the mounting rod. In some embodiments, the compression element may comprise a set screw having external threads for cooperating with complementary internal threads that are disposed on the proximal portion of the body.

A screw head receiving aperture of the body may be configured to engage with the screw head and permit polyaxial movement of the screw head within the screw head receiving aperture. In some embodiments the screw head receiving aperture is sized to securely receive the screw head.

The pressure cap may comprise a proximal end, a distal end, and a second mating element disposed on the distal end. Pressure cap may be configured to be disposed within the body and between the mounting rod and the screw. The pressure cap may be operable to exert pressure on the screw. In some embodiments, the proximal end of the pressure cap comprises a surface that is configured to align with a portion of the mounting rod (e.g., partially curved, V-shaped).

The second mating element of the pressure cap may be configured to mate with the first mating element of the screw and to limit the movement of the screw to that of a monoaxial screw. In some embodiments, the first mating element may comprise an internal recess and the second mating element may comprise an external protrusion. According to some embodiments, the first mating element may comprise an external protrusion and the second mating element may comprise an internal recess.

In some embodiments an external protrusion of a first mating element or a second mating element may comprise a protrusion base and a plurality of protrusion faces and an internal recess of corresponding mating element (second or first, respectively) may comprise a plurality of internal faces such that the plurality of protrusion faces may be configured to mate with the plurality of internal faces. The external protrusion of the first mating element or second mating element may have a width corresponding to the internal recess of the corresponding mating element (second or first, respectively), and a length sufficient to allow the internal recess to receive at least a portion of the external protrusion. In some embodiments the plurality of protrusion faces form a protrusion base with a polygonal shape. The polygonal shape of the protrusion base may be selected from the group consisting of a triangle, rectangle, pentagon, hexagon, heptagon, octagon, or star. In other embodiments the external protrusion may comprise a cube or right-rectangular prism segmented longitudinally by one or more arcs to form the protrusion base and the plurality of protrusion faces. In still other embodiments the external protrusion may comprise a cylinder segmented longitudinally by one or more arcs to form the protrusion base and the plurality of protrusion faces.

In some embodiments, a screw comprising a first mating element of an external protrusion may be a single structure. In other embodiments, a screw and a first mating element comprising an external protrusion may be separately manufactured and configured to be connectably modular. For example, a separate external protrusion may connectably attach to a screw head via assembly (e.g., snap connection, screw/threading connection, engaging undercuts and flexible tab structures, epoxy). According to some embodiments, a pressure cap comprising a second mating element of an external protrusion may be a single structure. In other embodiments, a pressure cap and a second mating element comprising an external protrusion may be separately manufactured and configured to be connectably modular. For example, a separate external protrusion may connectably attach to a distal end of a pressure cap via assembly (e.g., snap connection, screw/threading connection, engaging undercuts and flexible tab structures, epoxy).

According to another aspect of the disclosure, the spinal fixation system may further comprise a retention ring configured to be disposed within at least a portion of the screw head receiving aperture and operable to create a friction fit between an interior surface of the screw head receiving aperture and the screw head.

In some embodiments, a spinal fixation system may comprise a blocking ring disposed distal to the body and around at least a portion of the intermediate region of the screw. A blocking ring, according to some embodiments, may be rotatably connected to at least one of a screw and a body such that the blocking ring is configured to rotate around at least a portion of a circumference of the intermediate region. According to some embodiments, a blocking ring may comprise at least one of a slot extending between a distal surface and a proximal surface of the blocking ring and an indentation, each configured to direct the screw to pivot within restricted planes, including some embodiments restricting motion to a single plane.

In some embodiments of the present disclosure, the screw, the body, and the pressure cap each comprises a biocompatible material. According to some embodiments, the screw, the body, and the pressure cap each comprises a biocompatible material selected from the group consisting of titanium, titanium alloy, stainless steel, cobalt chrome, polyether ether ketone (PEEK), carbon fiber, nitinol, molybdenum rhenium alloy (Mo—Re), or any combination thereof.

The present disclosure relates, in some embodiments, to a method of affixing a spinal fixation system. In such embodiments the method may comprise engaging a screw within a body and securing the bone connection element of the screw in a bone. The method may further comprise selecting a pressure cap and mating a second mating element of the pressure cap with a first mating element of the screw head, limiting the movement of the screw to that of a monoaxial screw. The method may further comprise fitting a mounting rod within the mounting rod receiving channel so that the rod is disposed against the proximate end of the pressure cap. Further, the method may comprise securing a compression element within the mounting rod receiving channel so that a bias is applied by the mounting rod against the pressure cap.

The present disclosure relates, in some embodiments, to a method of affixing a spinal fixation system. In such embodiments the method may comprise fitting a screw within a tower. The method may further comprise securing a bone connection element of the screw in a bone. The method may further comprise selecting a pressure cap and mating a second mating element of the pressure cap with a first mating element of a screw head. Further, the method may comprise fitting a mounting rod within the mounting rod receiving channel so that the rod is disposed against a proximate end of the pressure cap. The method may further comprise securing a compression element within a mounting rod receiving channel of a body so that a bias is applied by a mounting rod against a pressure cap.

Any of the features, variations, and other embodiments described above for the articles and systems of the present disclosure may apply to the presently disclosed method without departing from there description herein.

BRIEF DESCRIPTION OF THE DRAWINGS

Some embodiments of the disclosure may be understood by referring, in part, to the present disclosure and the accompanying drawings, wherein:

FIG. 2B illustrates a perspective view of a screw engaged with a body and a blocking ring according to an embodiment of the disclosure;

FIG. 2C illustrates a perspective view of an underside of a blocking ring according to an embodiment of the disclosure;

DETAILED DESCRIPTION

Figure 1:
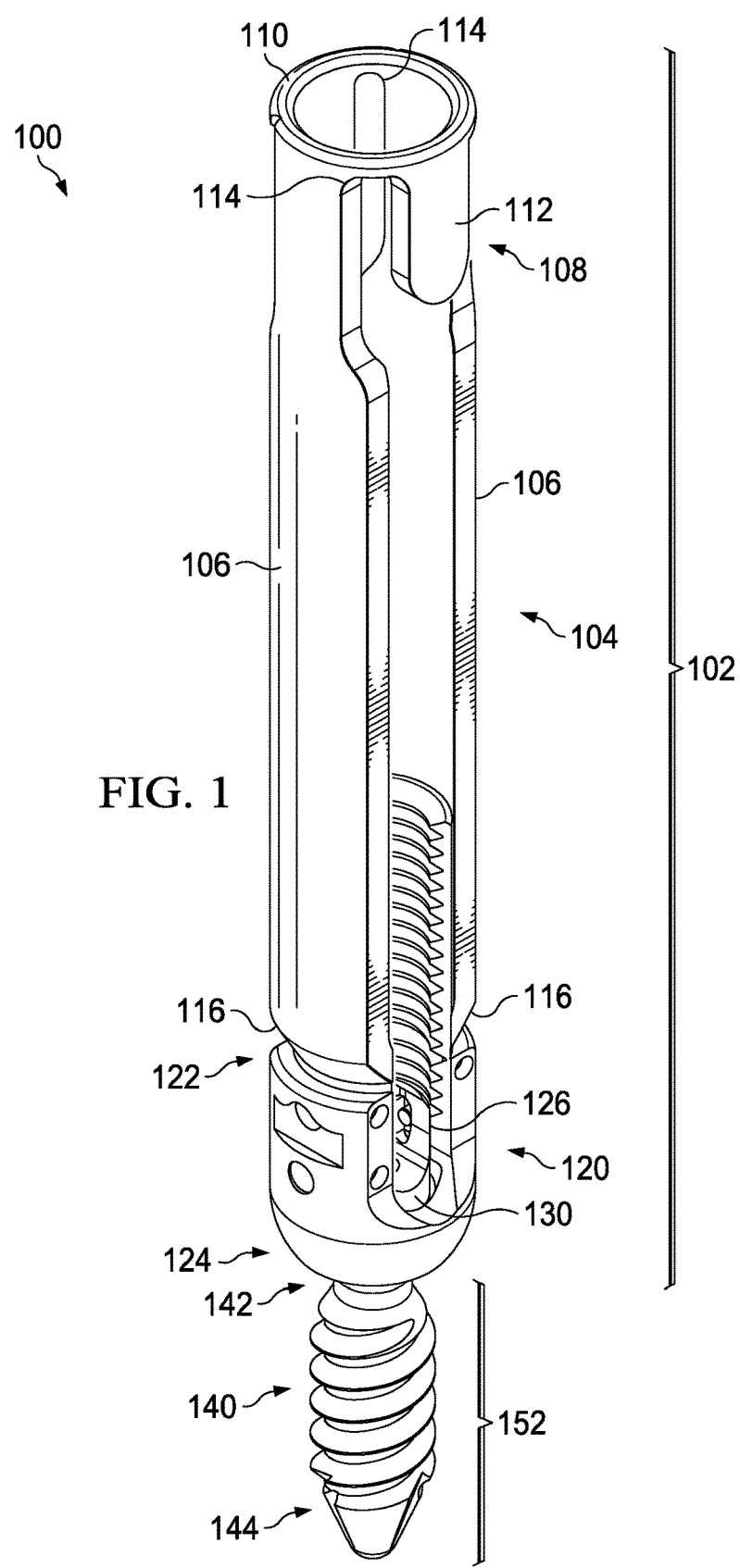
FIG. 1 illustrates a perspective view of a spinal fixation system according to an embodiment of the disclosure.

The present disclosure relates, in some embodiments, to spinal fixation systems in which a screw (e.g., 140, 240, 440, 840, 940) may be secured or fastened into a bone, for example, in the pedicle region of the spine. In some embodiments, screw (e.g., 140, 240, 440, 840, 940) may be secured into a bone in the cervical or iliac region of the spine. Screw (e.g., 140, 240, 440, 840, 940) may comprise a head (e.g. 446, 846, 946) disposed at a proximal end and a bone connection element (e.g., 152, 252, 452, 852) disposed at a distal end. In some embodiments, a first mating element (e.g., 448, 548, 848) is disposed on screw head (e.g., 446, 846, 946). A bone connection element (e.g., 152, 252, 452, 852) may be secured or fasted into a bone, in some embodiments. When affixed to a bone, a screw may be capable of various degrees of movement (e.g., polyaxial).

In some embodiments of the present disclosure a screw head (e.g., 446, 846, 946) engages with a tower (e.g., 102, 302). Such engagement of a screw head (e.g., 446, 846, 946) with a tower (e.g., 102, 302) may occur prior to or after insertion of bone connection element (e.g., 452, 852) into a bone.

Tower (e.g., 102, 302) may comprise a body (e.g., 120, 220, 320, 420, 520, 920) and an attachment portion (e.g., 104, 304). Body (e.g., 120, 220, 320, 420, 520, 920) may be distal to attachment portion (e.g., 104, 304) of a tower and may comprise a mounting rod receiving channel (e.g., 126, 326, 526) at a proximal end and a screw head receiving aperture (e.g., 130, 330, 430, 530) at a distal end. Screw head (e.g., 446, 846, 946) may engage with a body (e.g., 120, 220, 320, 420, 520, 920) of tower (e.g., 102, 302) via a screw head receiving aperture (e.g., 130, 330, 430, 530).

A spinal fixation system of the present disclosure may further comprise a pressure cap (e.g., 260, 360, 460, 560, 660, 760, 960) disposed within a body (e.g., 120) and configured to interact with a screw head (e.g., 446, 846, 946). A distal end of a pressure cap (e.g., 360, 460, 560, 660, 760, 960) may comprise a second mating element (e.g., 366, 466, 566, 666, 766, 966). In some embodiments of the present disclosure a second mating element (e.g., 366, 466, 566, 666, 766, 966) of a pressure cap (e.g., 360, 460, 560, 660, 760, 960) may interact with a screw head (e.g., 446, 846, 946) by mating with a first mating element (e.g., 448, 548, 848). Mating of second mating element (e.g., 366, 466, 566, 666, 766, 966) of a pressure cap (e.g., 360, 460, 560, 660, 760, 960) and a first mating element (e.g., 448, 548, 848) of a screw head (e.g., 446, 846, 946) may restrict the movement capabilities of a screw to that of a monoaxial screw. In such embodiments, a first mating element (e.g., 448) of a screw (e.g., 140) may comprise a geometry that substantially corresponds with the geometry that comprises a second mating element (e.g., 366) of a pressure cap (e.g., 360).

Embodiments of the present disclosure may advantageously provide for screws that can be converted from polyaxial to monoaxial capabilities. More specifically, the present disclosure relates, in some embodiments, to spinal fixation systems where a tower receives a pressure cap that is compatible with a screw such that mating of the pressure cap with the screw restricts the movement of the screw.

FIG. 1 illustrates a perspective view of spinal fixation system 100 according to an embodiment of the present disclosure. As seen in FIG. 1, spinal fixation system 100 may comprise a screw 140 and a tower 102. The proximal end 142 of screw 140 may engage with tower 102, while the distal end 144 of screw 140 extends out of tower 102 and may be secured into a bone. In some embodiments screw 140 may be first secured into a bone via bone connection element 152 and subsequently screw 140 may engage with tower 102.

Tower 102 may comprise body 120 and attachment portion 104. Attachment portion 104 and body 120 may be connected by one or more distal connection points 116 which may be frangible to allow separation of the attachment portion 104 from body 120. Distal connection points may be integrally formed between attachment portion 104 and body 120 but have sufficiently narrow width and height such that they may be readily broken or snapped. In some embodiments distal connection points 116 may further include grooves or carved areas to further control or promote breakage.

Attachment portion 104 may comprise two opposing arms 106 extending from the distal connection point 116 away from the body 120. Anti-splay apparatus 108 may be connected to the proximal end of arms 106 and comprise a ring shaped bridge 110 that joins the opposing arms 106 at a top surface of the arms. As seen in FIG. 1, in some embodiments, a portion of the bridge 110 may connect the upper portion or surface of arms 106.

Tabs 112 may extend upwardly or downwardly from the bridge 110 and be spaced from arms 106 by frangible connection points 114. As shown in FIG. 1, tabs 112 may have two parallel edges that run parallel to arms 106 with an end of the tab that is distal from the bridge being rounded. In some embodiments, tabs 112 may be curved along a longitudinal axis to mimic the shape of arms 106. Tabs 112 may take any of a number of shapes, including for example, square, oval, or semicircular. Frangible connection points 114 are integrally formed with bridge 110 but have sufficiently narrow width and height such that they may be readily broken or snapped. In some embodiments, frangible connection points 114 may have a width and/or height of no greater than 1 mm. According to some embodiments, the frangible connection points 114 may further include grooves or carved areas to further promote or control breakage. Other embodiments of anti-splay apparatuses (e.g., 108) are disclosed in U.S. Pat. No. 8,828,006 and are incorporated herein by reference.

As shown in FIG. 1, body 120 may comprise a proximal end 122 and a distal end 124. In some embodiments, body 120 may further comprise a mounting rod receiving channel 126 disposed at the proximal end 122 of body 120. According to some embodiments, a distal end 124 of body 120 of tower 102 may engage with proximal end 142 of screw 140. Engagement of body 120 with a proximal end 142 of screw 140 will be further described in the context of FIG. 2A, FIG. 4A, and FIG. 4B. Spinal fixation system 100 may further comprise a pressure cap 360 (e.g., FIG. 3) and retention ring 384 (e.g., FIG. 3).

Figure 2A:
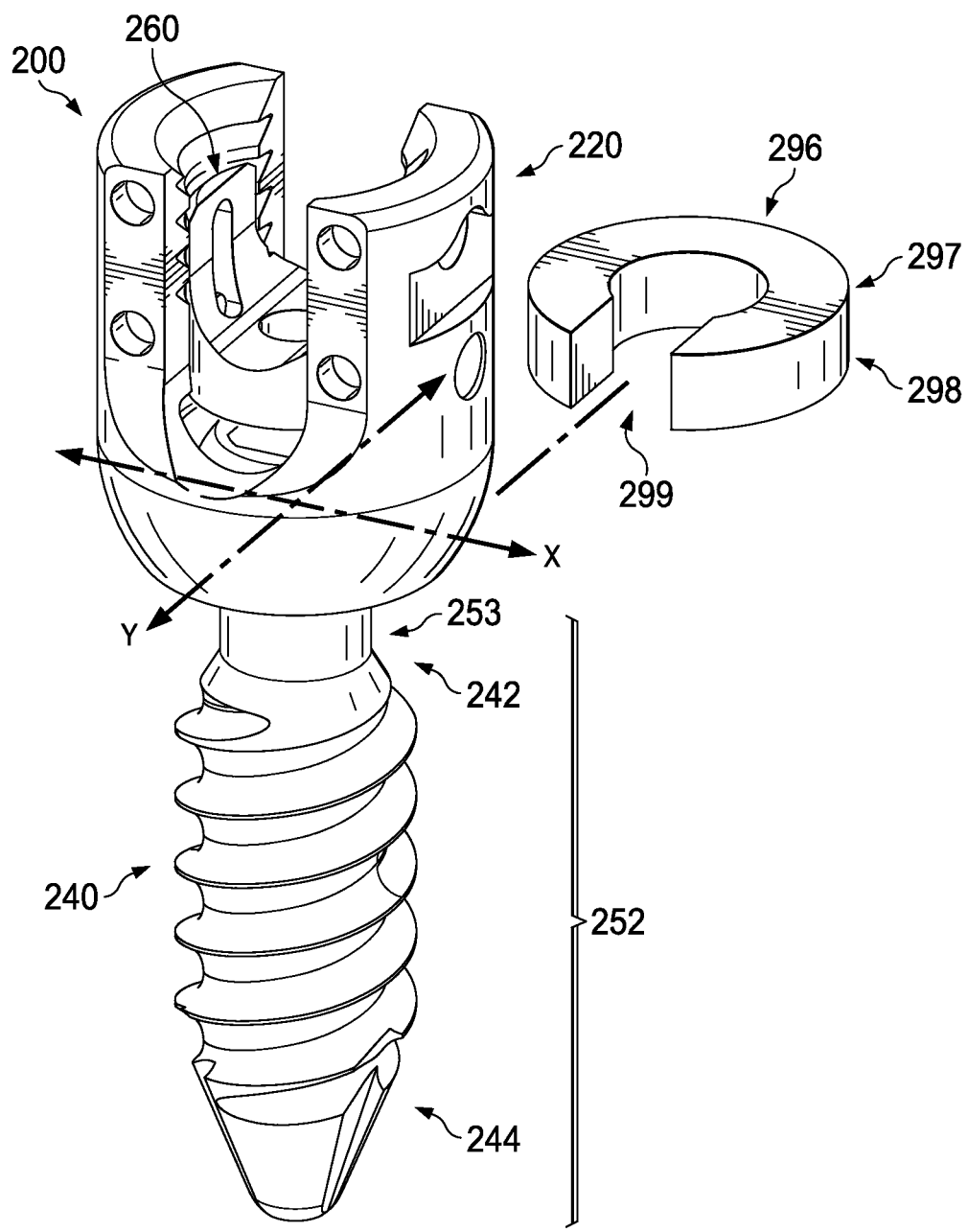
FIG. 2A illustrates a perspective view of a screw engaged with a body and a blocking ring disengaged from the screw/body according to an embodiment of the disclosure.

FIG. 2A illustrates a perspective view of a system 200 comprising a screw 240 engaged with a body 220 according to an embodiment of the disclosure. In some embodiments, screw 240 may comprise a head disposed at a proximal end 242 and a bone connection element 252 disposed towards a distal end 244. As shown in FIG. 2A, screw 240 may further comprise an intermediate region 253 disposed between head and bone connection element 252. A proximal end 242 of screw 240 may engage with body 220, while a distal end 244 of screw 240 extends out of body 220 and may be secured into a bone via a bone connection element 252. Proximal end 242 of screw 240 may engage with body 220 such that screw 240 is capable of polyaxial movement. As shown in FIG. 2A, in some embodiments, screw 240 can rotate within body 220 in multiple axes (FIG. 2A, reflecting movement capabilities along both the X and Y axes). In some embodiments body 220 may be part of tower 102 (e.g., FIG. 1).

Spinal fixation system 200 may further comprise a pressure cap 260. Pressure cap 260 may be inserted within body 220 such that a distal end of pressure cap 260 contacts a proximal end 242 of screw 240. As shown in FIG. 2A, in some embodiments, screw 240 will be capable of polyaxial movement within body 220 despite contact between a distal end of pressure cap 260 and a proximal end 242 of screw 240. In other embodiments (e.g., FIG. 4A, 4B, 5A, 5B, 9) contact between a distal end of pressure cap 260 and a proximal end 242 of screw 240 may restrict movement capabilities of screw 240 to that of a monoaxial screw.

FIG. 2A further illustrates a blocking ring 296 that is disengaged from body 220 and screw 240. Blocking ring 296 may comprise a proximal surface 297 and a distal surface 298. As shown in FIG. 2A, in some embodiments, blocking ring 296 further comprises at least one slot 299 extending between a distal surface 298 and a proximal surface 297 of blocking ring 296. In some embodiments slot 299 extends the entire length between distal surface 298 and proximal surface 297 of blocking ring 296, thus forming a C-shape as shown in FIG. 2A. In other embodiments, slot 299 extends at least one-quarter, or one-third, or one-half, or two-thirds, or three-quarters of the length between distal surface 298 and proximal surface 297 of blocking ring 296. In some embodiments, blocking ring 296 may comprise indentations in a distal surface 298 or an underside (e.g., FIG. 2C). Engagement of blocking ring 296 with a body 220 will be further described in the context of FIG. 2B.

FIG. 2B illustrates a perspective view of a system 200 comprising a screw 240 engaged with a body 220 and a blocking ring 296 according to an embodiment of the disclosure. Blocking ring 296 may be disposed distal to body 220. Blocking ring 296 may comprise a proximal surface 297 and a distal surface 298. In some embodiments, blocking ring 296 further comprises at least one slot 299 extending between a distal surface 298 and a proximal surface 297. In operation, screw 240 is operable to pivotally move within restricted planes or a single plane as defined by slot 299. In some embodiments, as shown in FIG. 2B, slot 299 extends the entire length between a distal surface 298 and a proximal surface 297 of blocking ring 296. In other embodiments, slot 299 extends at least one-quarter, or one-third, or one-half, or two-thirds, or three-quarters of the length between a distal surface 298 and a proximal surface 297 of blocking ring 296. In some embodiments, screw 240 has about 0 degrees to about 90 degrees of pivotal movement within the plane or planes of slot 299.

In some embodiments, screw 240 may comprise a head disposed at a proximal end 242 and a bone connection element 252 disposed towards a distal end 244. As shown in FIG. 2B, screw 240 may further comprise an intermediate region 253 disposed between head and bone connection element 252. A surface of intermediate region 253 of screw 240 may comprise any number of textures without departing from this disclosure (e.g., smooth, threaded).

According to some embodiments, blocking ring 296 may be disposed around at least a portion of intermediate region 253 of screw 240. In some embodiments, blocking ring 296 may be disposed directly adjacent to body 220. In other embodiments, blocking ring 296 may be disposed distal to body 220 such that blocking ring 296 and body 220 are not in direct contact. Blocking ring 296, in some embodiments, may be configured to rotate around at least a portion of intermediate region 253 of screw 240, independently of screw 240 and body 220 such that the rotation of blocking ring 296 aligns slot 299 with a desired plane in which screw 240 may pivot.

In some embodiments, blocking ring 296 may be rotatably connected to screw 240, body 220, or both. According to some embodiments of the disclosure blocking ring 296 may be rotatably connected to screw 240, body 220, or both by a snap connection, a screw/threading connection, engagement of undercuts and flexible tab structures, or any combination thereof. For example, a blocking ring 296 may comprise flexible tab structures capable of engaging with corresponding undercuts on the screw 240 or body 220. In some embodiments, blocking ring 296 may be configured to rotate between 0 degrees and 360 degrees around an intermediate region 253 of screw 240.

In some embodiments a blocking ring may be comprised of a biocompatible material, such as titanium, titanium alloy, stainless steel, cobalt chrome, polyether ether ketone (PEEK), carbon fiber, nitinol, molybdenum rhenium alloy (Mo—Re), or any combination thereof.

FIG. 2C illustrates a perspective view of an underside of a blocking ring 296 according to an embodiment of the disclosure. In some embodiments, blocking ring 296 may comprise one or more indentations 295 in a proximal surface 297, a distal surface 298, on an underside, or any combination thereof. Indentation 295 may enable pivotal movement of a screw 240 (e.g., FIG. 2B) within a plane 293 of indentation 295. For example, as shown in FIG. 2C, blocking ring 296 may comprise two indentations 295 disposed across from one another on opposing sides of an underside of blocking ring 296. Such embodiments may enable a screw 240 (e.g., FIG. 2A) to pivot within plane 293 of the opposing indentations 295, but would restrict screw 240 from pivoting within any other plane.

In some embodiments indentation 295 may comprise a wedge, a slit, or a series of slits in an underside and/or distal surface 298 of blocking ring 296. Persons skilled in the art will understand that various configurations of blocking ring 296 are within the scope of the current disclosure, including those comprising one or more slots 299, one or more indentations 295, or any combination thereof configured to permit pivotal movement of a screw 240 within a plane 293 of the slot or indentation.

Figure 3:
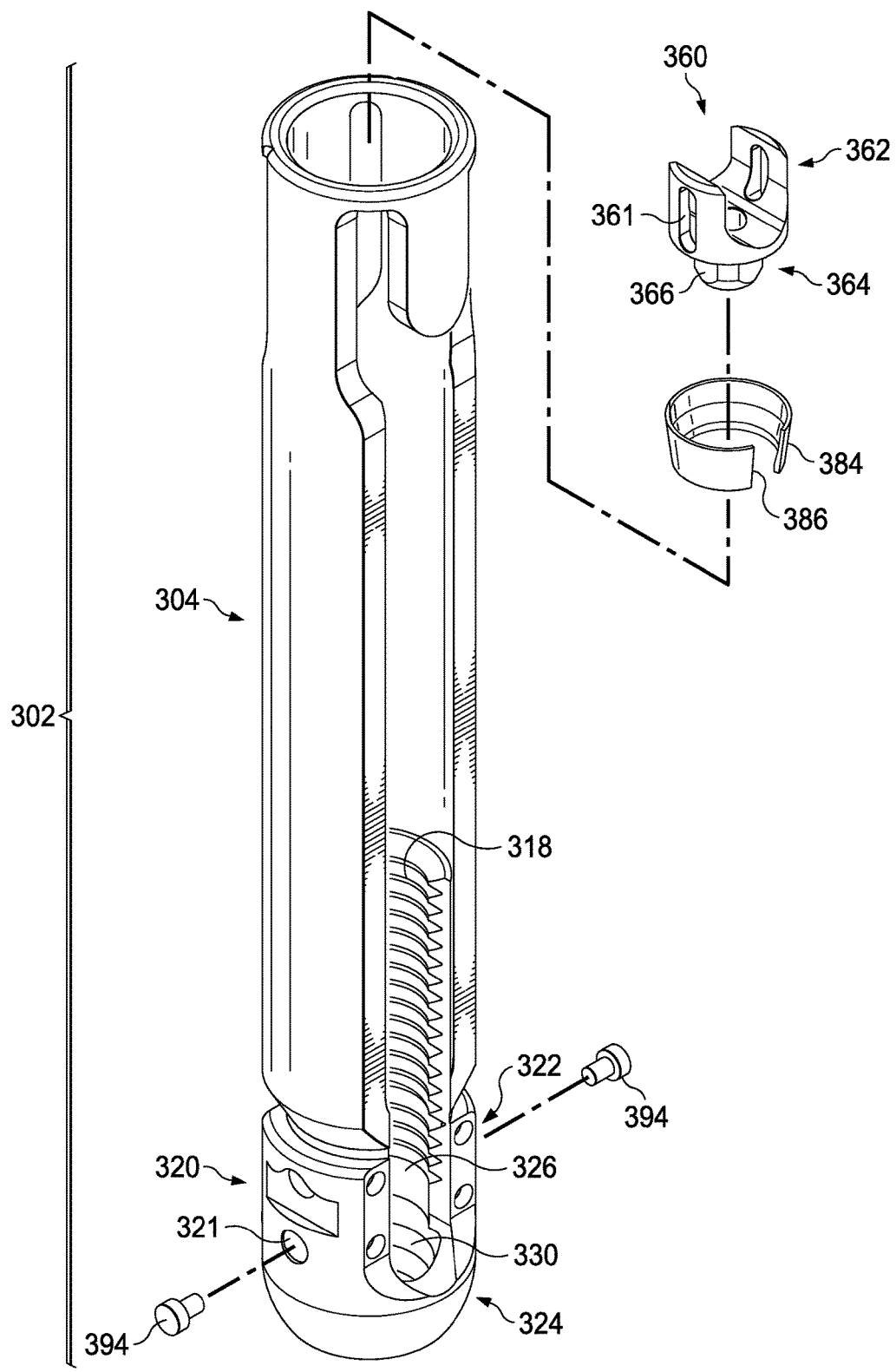
FIG. 3 illustrates a perspective view of a spinal fixation system with a pressure cap and retention ring disengaged from a tower according to an embodiment of the disclosure.

FIG. 3 illustrates a perspective view of a tower 302, a pressure cap 360, and a retention ring 384 according to an exemplary embodiment of the disclosure. Tower 302 may comprise a body 320 and an attachment portion 304. In some embodiments, as shown in FIG. 3, tower may further comprise internal threading 318. Internal threading 318 may extend along the entire length of tower 302 or may extend only along a distal portion of tower 302. In some embodiments internal threading 318 may extend from a distal portion of attachment portion 304 to a proximal portion of body 320. In some embodiments internal threading 318 may be configured to receive a compression element 992 (e.g., FIG. 9). The dimensions, pattern, and structure of internal thread 318 may be varied to achieve different effects or provide different advantages without departing from the description herein. For example, different internal threads 318 may allow for compression elements with different external thread to be secured on a proximal end of body 320. It is understood that threads 318 may also be replaced with ridges, thus allowing a compression-element to snap-fit into place. In other embodiments, tower may comprise a smooth or mostly smooth interior surface. Different compression elements may be more advantageous depending on the type of stability needed or the intended anatomic location of a spinal fixation system.

A body 320 of the present disclosure may comprise a proximal end 322 and a distal end 324 disposed along a longitudinal axis. In some embodiments, a mounting rod receiving channel 326 may be disposed at proximal end 322 of body 320. A screw head receiving aperture 330 may be disposed at distal end 324 of body 320, according to some embodiments. Body 320 may further comprise two body pin holes 321 disposed across from one another on opposing walls of body 320.

Figure 4A:
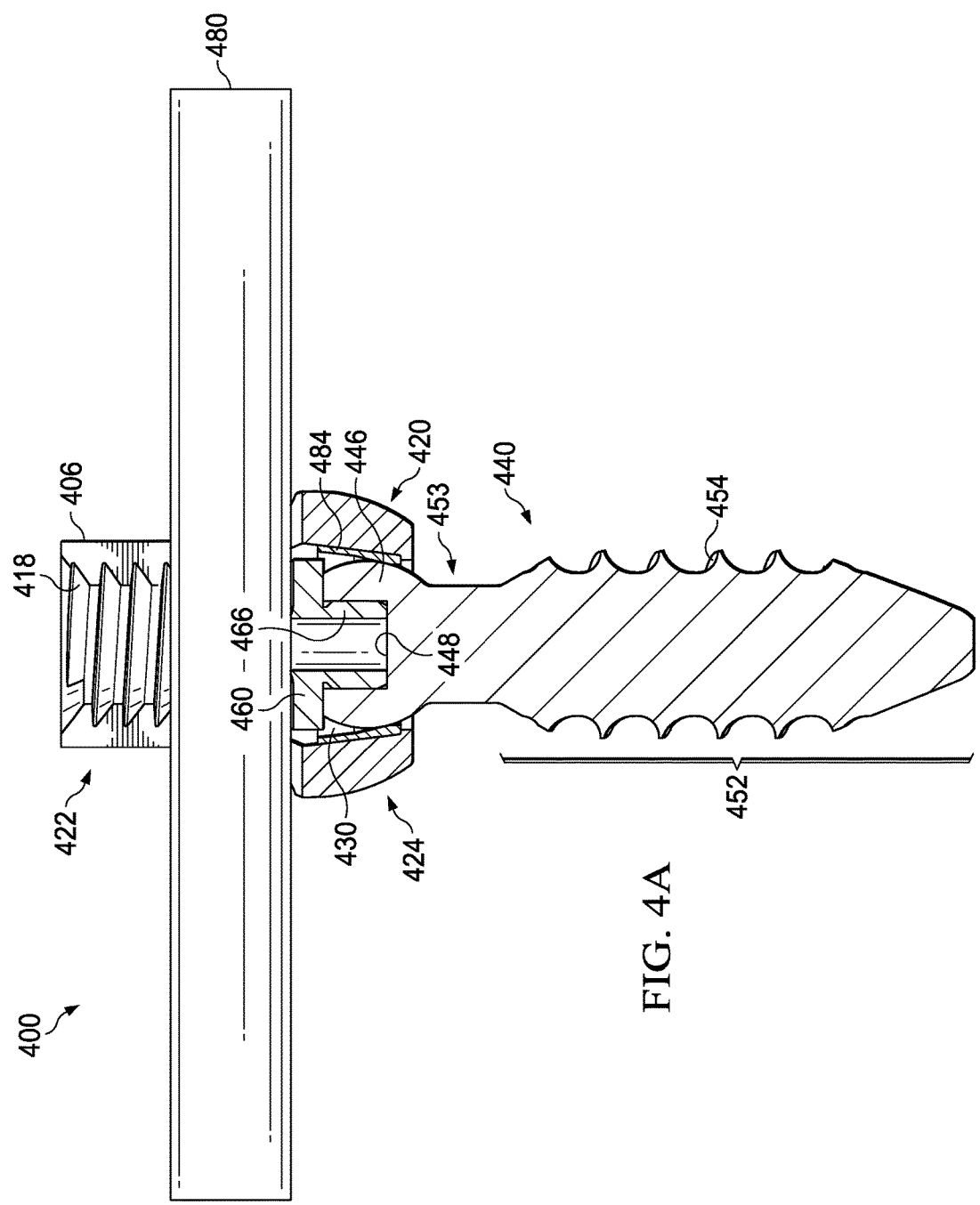
FIG. 4A illustrates a cross-sectional view of a spinal fixation system fitted together according to an exemplary embodiment of the disclosure.

Mounting rod receiving channel 326 disposed at proximal end 322 of body 320 may be operable to receive a mounting rod 480 (e.g., FIG. 4A). Mounting rod 480 (e.g., FIG. 4A) may be received in an orientation such that the mounting rod may be substantially orthogonal to the longitudinal axis of body 320. As shown in FIG. 3, internal threading 318 may extend into mounting rod receiving channel 326. In some embodiments internal threading 318 may extend along the entire length of the mounting rod receiving channel. In other embodiments, internal threading 318 may extend along one-eighth, or one-sixth, or one-fourth, or one-half, or two-thirds, or three-quarters of a length between a proximal end and a distal end of the mounting rod receiving channel. In some embodiments internal threading 318 may be configured to receive a compression element 992 (e.g., FIG. 9).

A screw head receiving aperture 330 disposed at distal end 324 of body 320 may be operable to receive head 446 (e.g., FIG. 4A) of pedicle screw 440 (e.g., FIG. 4A). In some embodiments, a screw head receiving aperture 330 may have a tapered shape that narrows at a distal end of screw head receiving aperture 330 to fit against a screw head 446 (e.g., FIG. 4A). In some embodiments, an interior surface of screw head receiving aperture 330 may be lined with a retention ring 384. As illustrated in FIG. 3, a retention ring 384 may be inserted into screw head receiving aperture 330 through tower 302. Retention ring 384 may facilitate retention of screw head 446 (e.g., FIG. 4A) within a screw head receiving aperture 330. In some embodiments, retention ring 384 may be composed of a softer grade of material than a material composition of body 320 and may provide a friction fit between screw head receiving aperture 330 and screw head 446 (e.g., FIG. 4). In some embodiments retention ring 384 may comprise at least one slot 386. Slot 386 of retention ring 384 may be configured to allow increased flexibility of retention ring 384 and to permit a head 446 of screw 440 (e.g., FIG. 4) to pass through the retention ring 384, thus attaching a body 320 to the screw while still permitting pivotal movement there between.

The dimensions of body 320 may be varied to achieve different effects or provide different advantages without departing from the description herein. In some embodiments, a height of body 320 may range from about 7 mm to about 30 mm. Various advantages may be derived from selecting an appropriately sized body 320. In some embodiments, a larger body 320 may be advantageous so that the larger body size may accommodate larger pressure caps, larger mounting rods, or larger compression elements. In some embodiments, a smaller body 320 may be advantageous so that the smaller body size may be less invasive as part of the spinal fixation system in the patient's body and may provide a lower profile implant against the patient's spine.

As shown in FIG. 3, a pressure cap 360 may be inserted at a proximal end of tower 302 and disposed at the distal end 324 of a body 320. Pressure cap 360 may comprise proximal end 362 and distal end 364 along a longitudinal axis. Distal end 364 of pressure cap 360 may be inserted into tower 302 and disposed at a distal end 324 of body 320. Pressure cap 360 may comprise a second mating element 366 disposed on distal end 364 and configured to mate with screw 140 (e.g., FIG. 1). In some embodiments, pressure cap 360 may be fixed within body 320 in a position adjacent to screw 140 (e.g., FIG. 1). As shown in FIG. 3, a second mating element 366 may be configured as an external protrusion. In some embodiments, as shown in FIG. 4B, a second mating element may be configured as an internal recess.

Pressure cap 360 may further comprise two pressure cap pin holes 361 disposed across from one another on opposing walls of pressure cap 360. In some embodiments, when a pressure cap is fixed within body 320 in a position adjacent to screw 140 (e.g., FIG. 1), body pin holes 321 and pressure cap holes 361 align such that a holding pin 394 may be received there through. As shown in FIG. 3, one holding pin 394 may be disposed within each of the two aligned body pin holes 321 and pressure cap pin holes 361. A holding pin 394 may restrict or prevent longitudinal movement of the pressure cap 360 which may allow the pressure cap 360 to apply a bias against the head (e.g., FIG. 4A 446) of the screw (e.g., FIG. 4A 440).

Figure 4B:
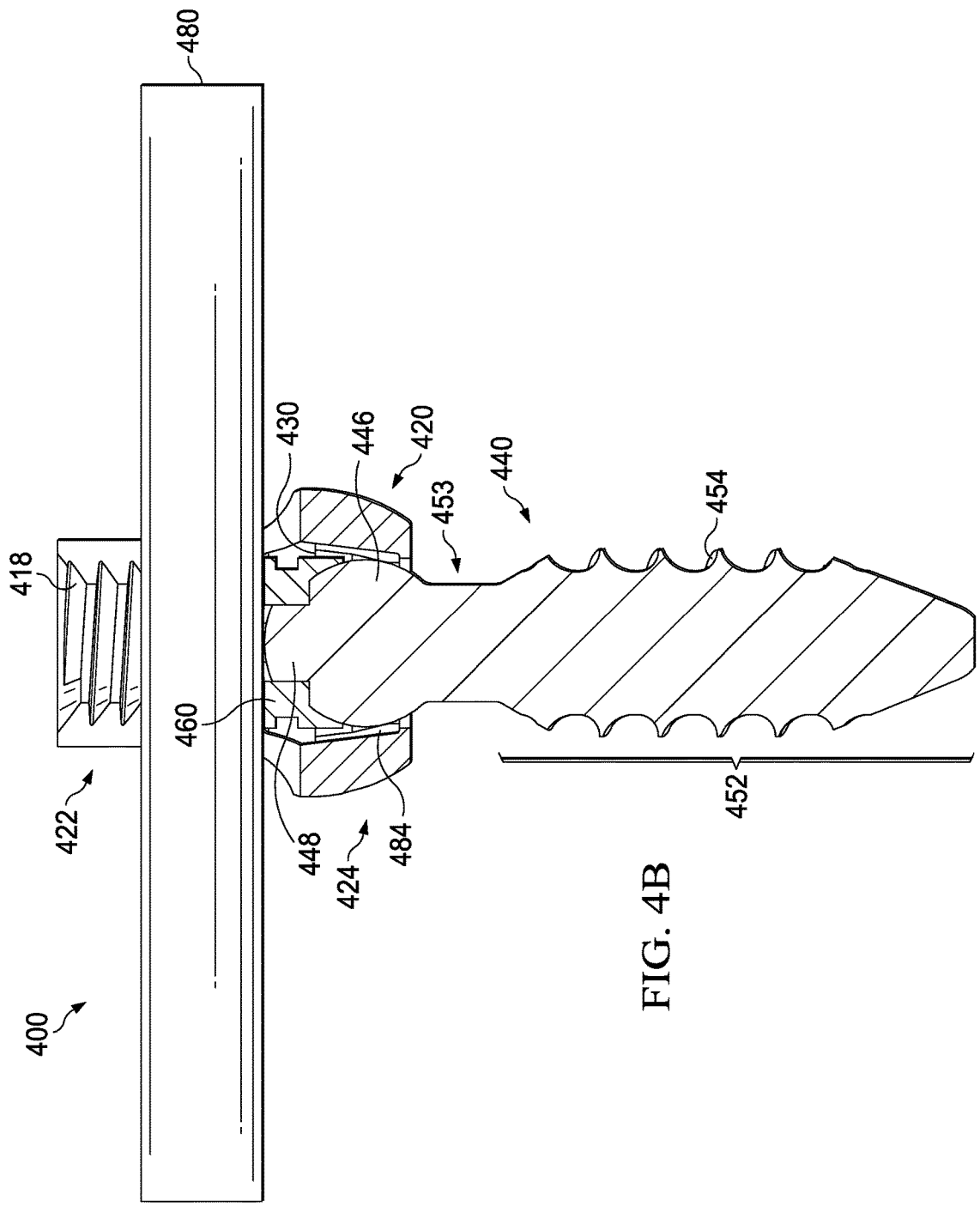
FIG. 4B illustrates a cross-sectional view of a spinal fixation system fitted together according to an exemplary embodiment of the disclosure.

FIGS. 4A and 4B illustrate cross-sectional views of spinal fixation systems 400 fitted together according to exemplary embodiments of the disclosure. As seen in FIG. 4A and FIG. 4B, spinal fixation system 400 may comprise a screw 440, a body 420, and a mounting rod 480. A screw 440 may comprise a screw head 446 disposed at a proximal end of screw 440 and a bone connection element 452 disposed towards a distal end of screw 440. According to some embodiments, a screw 440 may further comprise an intermediate region 253 disposed between screw head 446 and body connection element 452. In some embodiments, bone connection element 452 of screw 440 may comprise external thread 454. In some embodiments, external thread 454 may be secured into a portion of a spinal bone (e.g., pedicle region, iliac region, cervical region). When the spinal fixation system 400 is attached to a bone, the body 420 may be capable of various degrees of movement (e.g., polyaxial) (e.g., FIG. 2A). In some embodiments screw head 446 may have a spherical surface. A first mating element 448 may be disposed on head 446 of screw 440.

As seen in FIG. 4A and FIG. 4B, a body 420 of the present disclosure may comprise a proximal end 422 and a distal end 424 disposed along a longitudinal axis of body 420. A proximal end 422 of body 420 may be frangibly connected to arms 106 of a tower 102 (e.g., FIG. 1). A mounting rod receiving channel 326 (e.g., FIG. 3) may be disposed at a proximal end 422 of body 420. A screw head receiving aperture 430 may be disposed at distal end 424 of body 420.

In some embodiments, a screw head receiving aperture 430 disposed at distal end 424 of body 420 may be operable to receive head 446 of screw 440. As shown in FIG. 4A and FIG. 4B, in some embodiments a screw head receiving aperture 430 may have a tapered shape that narrows at the distal end of pedicle head receiving aperture 430 to fit against pedicle screw head 446. According to some embodiments, a retention ring 484 may line an interior surface of pedicle screw head receiving aperture 430 and facilitate retention of screw head 446 within screw head receiving aperture 430. In some embodiments, retention ring 484 may be composed of a softer grade of material than the material composition of body 420 and may provide a friction fit between screw head receiving aperture 430 and screw head 446.

Figure 9:
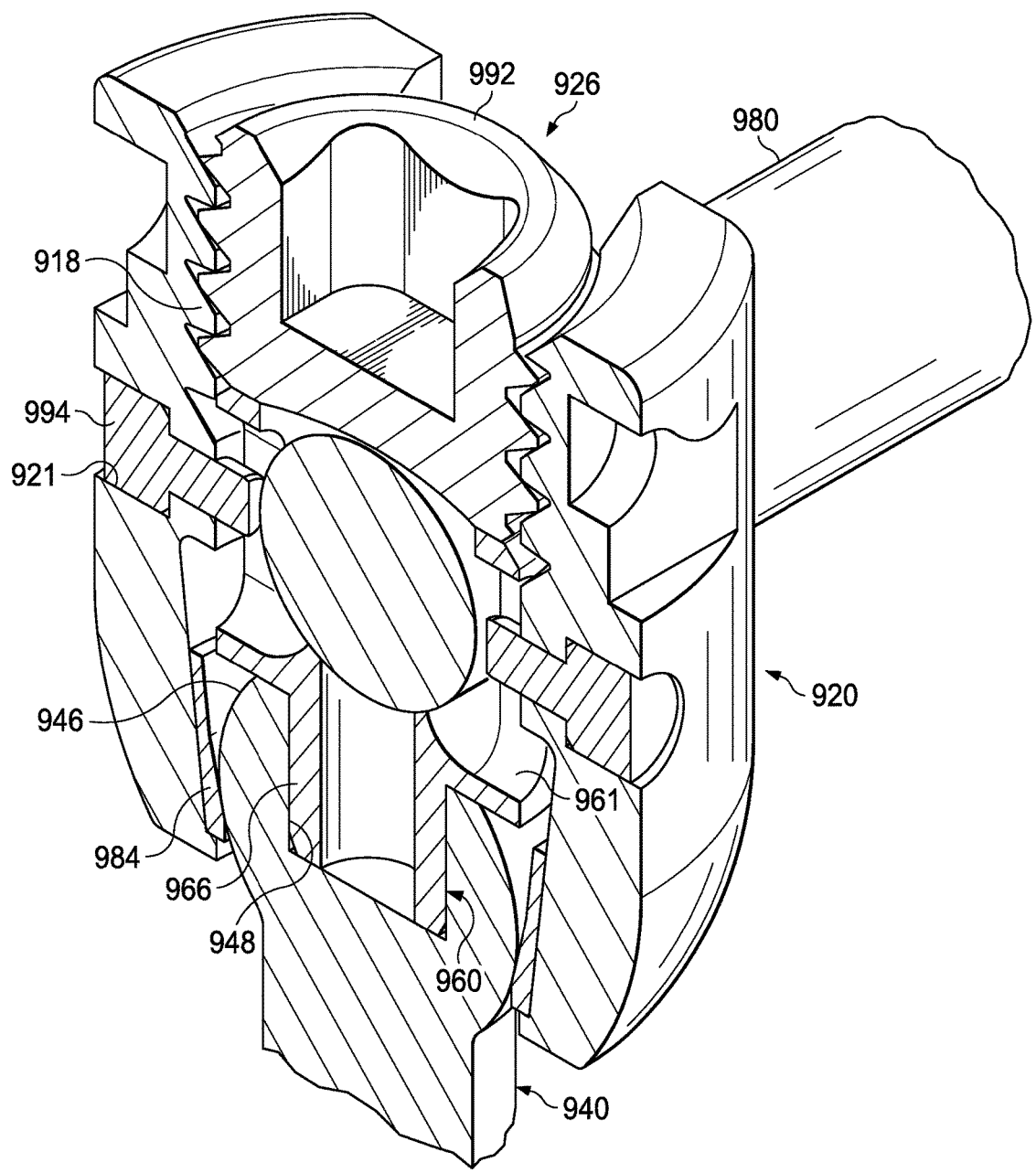
FIG. 9 illustrates a profile view of a mounting rod, a pressure cap, a body, and a screw fitted together according to an exemplary embodiment of the disclosure.

Screw 440 and body 420 may be selected such that screw head receiving aperture 430 may be sized to securely receive head 446 of screw 440. According to some embodiments of the present disclosure, screw head receiving aperture 430 may receive head 446 such that spherical surface, as seen in FIG. 9, may be substantially enclosed by screw head receiving aperture 430. As a result, the contact between screw head receiving aperture 430 and spherical surface of screw head 446 may create a secure connection between screw 440 and body 420. Persons having ordinary skill in the art will appreciate that a spherical surface of screw head 446 may not need to be substantially enclosed in order to create a secure connection between screw 440 and body 420.

According to some embodiments of the present disclosure, a screw head receiving aperture 430 may receive screw head 446 such that a first mating element 448 may be substantially exposed and a second mating element 466 of pressure cap 460 may mate with or be secured therein.

According to some embodiments of the present disclosure, a screw head receiving aperture 430 may receive screw head 446 through a variety of means. For example, in some embodiments, a screw 440 may be lowered into body 420 so that screw head 446 may directly rest in screw head receiving aperture 430. In other embodiments, a screw head receiving aperture 430 of body 420 may be lowered onto the screw head 446. Any number of mechanisms may be used to engage screw head receiving aperture 430 with head 446 of screw 440. The mechanism may be varied without departing from the description herein.

As shown in FIG. 4A, a first mating element 448 may comprise an internal recess disposed on screw head 446, in some embodiments. As shown in FIG. 4B, a first mating element 448 may comprise an external protrusion disposed on screw head 446, according to some embodiments. A first mating element 448 of screw 440 may be configured to mate with the second mating element 466 of pressure cap 460 thereby limiting the pivotal movement of the screw to that of a monoaxial screw (e.g., FIG. 2B).

A spinal fixation system 400 may further comprise pressure cap 460 disposed within body 420 and seated adjacent to screw head 446. In some embodiments, a second mating element 466 disposed on a distal end of a pressure cap 460 may be configured to mate with a first mating element 448 of screw 440. As illustrated in FIG. 4A, a second mating element 466 may comprise an external protrusion configured to mate with an internal recess configuration of a first mating element 448. As illustrated in FIG. 4B, a second mating element 466 may comprise an internal recess configured to mate with an external protrusion of a first mating element 448.

In some embodiments, a mounting rod receiving channel 326 (e.g., FIG. 3) of body 420 may be operable to receive a mounting rod 480. The mounting rod 480 may be received in an orientation such that the mounting rod may be substantially orthogonal to the longitudinal axis of body 400. Mounting rod 480 may be disposed against a proximate end of a pressure cap 460. In some embodiments, a proximal end of pressure cap 460 may be configured to align with a surface of a mounting rod 480. For example, a proximal end of a pressure cap 460 may be curved, partially curved, or V-shaped such that at least a portion of a surface of the proximal end aligns with a surface of a mounting rod. In some embodiments, a mounting rod receiving channel 326 (e.g., FIG. 3) may further comprise a proximal portion comprising an internal thread 418. An internal thread 418 may be operable to receive a compression element 992 (e.g., FIG. 9). A compression element 992 (e.g., FIG. 9) may be secured within a mounting rod receiving channel 326 (e.g., FIG. 3) adjacent to a mounting rod 480 such that the mounting rod 480 is biased against and/or exerts a compressive force against a pressure cap 460. A bias and/or compressive force exerted against a pressure cap 460 may secure a connection of a first mating element 448 with a second mating element 466.

Figure 5A:
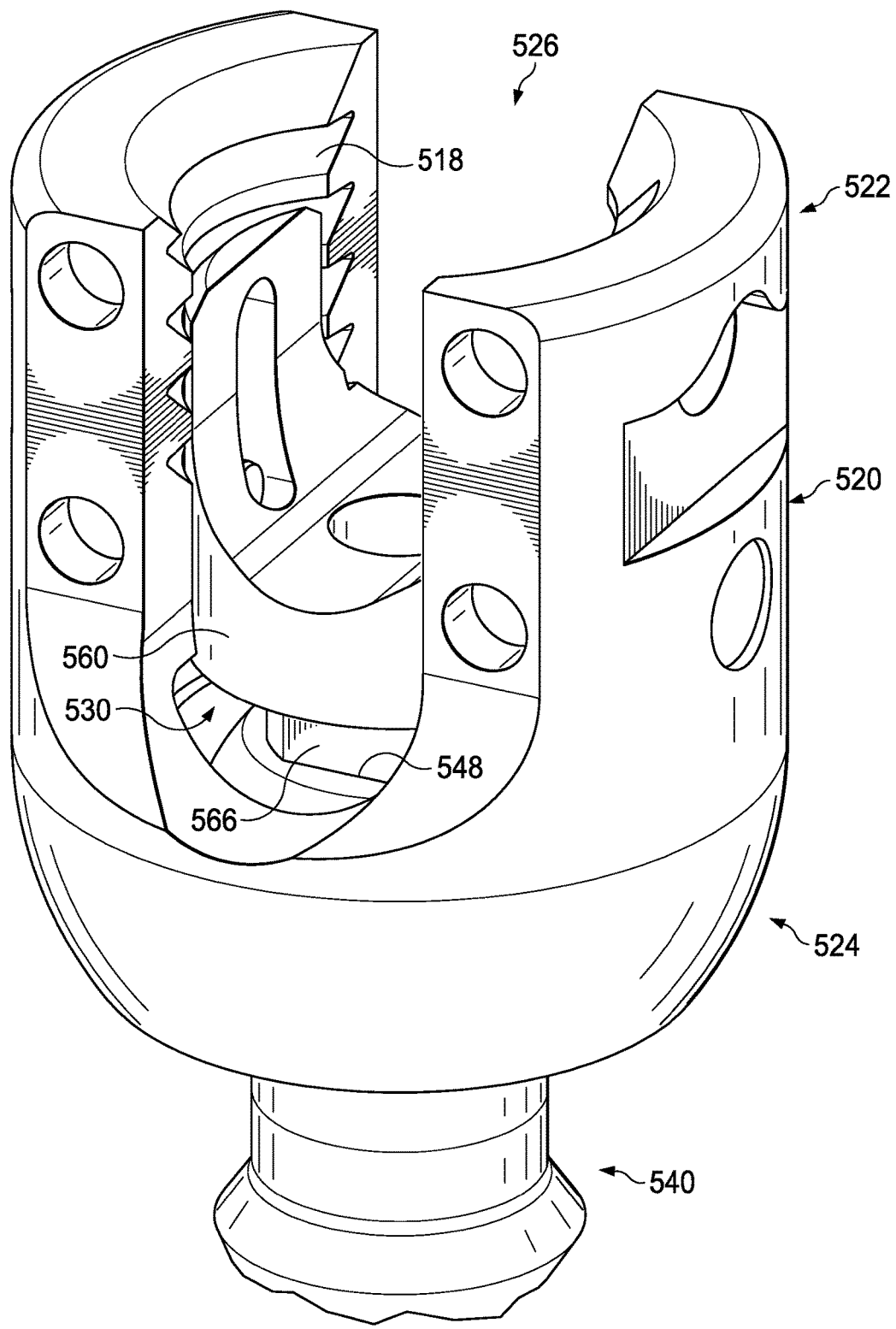
FIG. 5A illustrates a perspective view of a body engaged with a screw and a pressure cap in a disengaged position according to an exemplary embodiment of the disclosure.
Figure 5B:
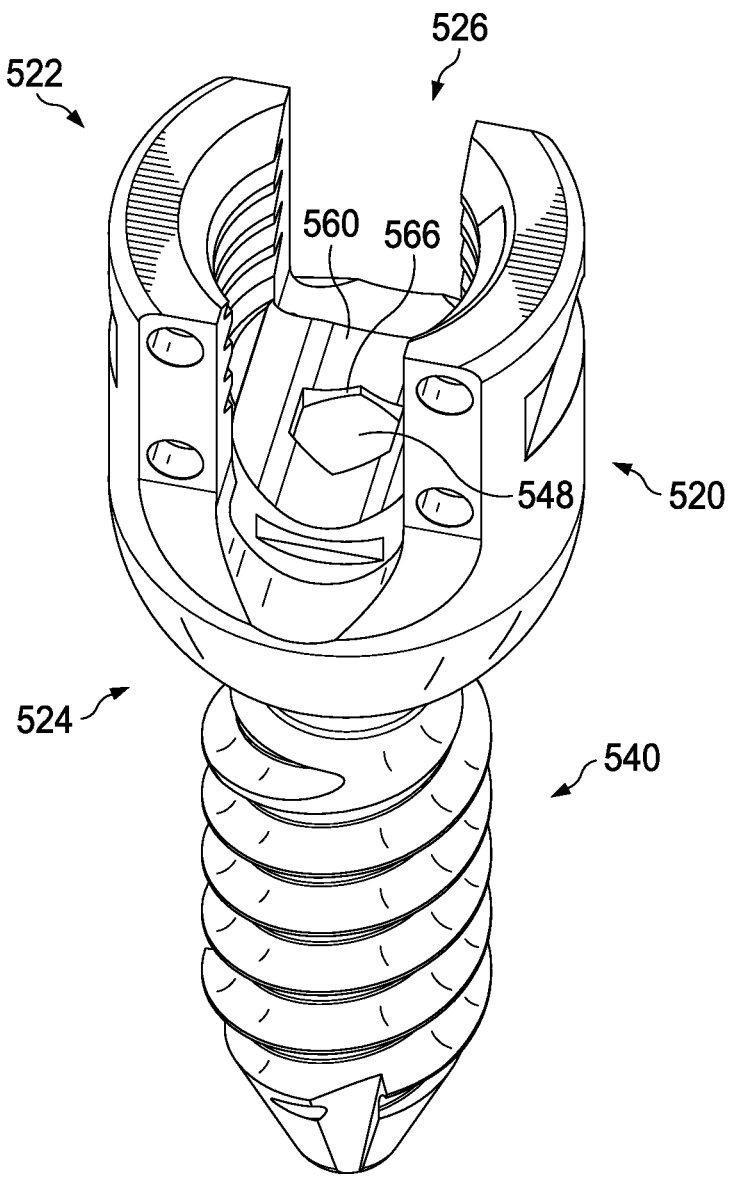
FIG. 5B illustrates a perspective view of a body engaged with a screw and a pressure cap in an engaged position according to an exemplary embodiment of the disclosure.

FIGS. 5A and 5B illustrate perspective views of a body 520 and a screw 540 engaged with each other according to specific example embodiments of the disclosure. A screw 540 may comprise head 446 (e.g., FIG. 4) at a proximal end 142 (e.g., FIG. 1) and bone connection element 452 (e.g., FIG. 4) at distal end 144 (e.g., FIG. 1). Further, a first mating element 548 may be disposed on a head 446 (e.g., FIG. 4A) of screw 540. As shown in FIG. 5A, a first mating element 548 may comprise an internal recess. In some embodiments, as shown in FIG. 5B, a first mating element 548 may comprise an external protrusion.

As shown in FIG. 5A and FIG. 5B, body 520 of the present disclosure may comprise a proximal end 522 and a distal end 524 disposed along a longitudinal axis. In some embodiments, a mounting rod receiving channel 526 may be disposed at proximal end 522 of body 520. A screw head receiving aperture 530 may be disposed at a distal end 524 of body 520.

A mounting rod receiving channel 526 disposed at proximal end 522 of body 520 may be operable to receive mounting rod 480 (e.g., FIG. 4A), according to some embodiments. In some embodiments, as shown in FIG. 5A and FIG. 5B, a mounting rod receiving channel 526 may comprise internal threading 518 configured to receive a compression element 992 (e.g., FIG. 9).

A screw head receiving aperture 530 disposed at a distal end 524 of body 520 may be operable to receive and engage with a head 446 (e.g., FIG. 4A) of a screw 540. Screw 540 and body 520 may be selected such that screw head receiving aperture 530 may be sized to securely receive head 446 (e.g., FIG. 4A) of screw 540. In some embodiments, a screw head receiving aperture 530 may also receive a retention ring 484 (e.g., FIG. 4A) such that there is a friction fit between a screw head 446 (e.g., FIG. 4A) and the screw head receiving aperture 530. In some embodiments a screw head receiving aperture 530 may receive screw head 446 (e.g., FIG. 4A) such that a first mating element 548 may be substantially exposed.

According to some embodiments, a screw head 446 (e.g., FIG. 4A) may engage with a screw head receiving aperture 530 such that screw 540 is capable of polyaxial movement. For example, in some embodiments, a screw head receiving aperture 530 may engage with a head 446 (e.g., FIG. 4A) of screw 540 in the manner of a ball and socket joint. A spherical surface of a head 546 of screw 540 may be allowed to freely rotate within screw head receiving aperture 530 (see e.g., FIG. 2B). Persons having ordinary skill in the art would appreciate that the type of screw 540 and type of body 520 chosen may determine what range of motion or how many degrees of freedom a head 446 (e.g., FIG. 4A) of screw 540 may have in screw head receiving aperture 530.

The dimensions of a body 520 may be varied to achieve different effects or provide different advantages without departing from the description herein. In some embodiments, a height between a proximal end and a distal end of a body may range from about 7 mm to about 30 mm. Various advantages may be derived from selecting an appropriately sized body 520. In some embodiments, a larger body 520 may be advantageous so that the larger body size may accommodate larger pressure caps, larger mounting rods, or larger compression elements. In some embodiments, a smaller body 520 may be advantageous so that the smaller body size may be less invasive as part of the spinal fixation system in the patient's body and may provide a lower profile implant against the patient's spine.

The dimensions of screw 540 may be varied to achieve different effects or provide different advantages without departing from the description herein. Screws 540 with different sized heads 546, as defined by the radius of spherical surfaces, may be more appropriate in different circumstances. For example, a screw 540 used for the cervical and upper thoracic regions may have a smaller head 546 or a smaller radius for the spherical surface of head 846 (e.g., FIG. 8). As another example, screw 540 used for the lumbar or lower thoracic regions may have a larger head 546 or a larger radius for the spherical surface of head 546.

FIG. 5A and FIG. 5B further illustrate perspective views of a pressure cap 560 inserted within a mounting rod receiving channel 526 of a body 520. A pressure cap 560 may comprise a proximal end 362 (e.g., FIG. 3) and a distal end 364 (e.g., FIG. 3) along a longitudinal axis. A distal end 364 (e.g., FIG. 3) of pressure cap 560 may be inserted into a mounting rod receiving channel 526 and travel from a proximal end 522 of body 520 towards a distal end 524 of body 520. In some embodiments, a second mating element 566 may be disposed on a distal end 564 of pressure cap 560. A second mating element 566 of pressure cap 560 may be configured to mate with a first mating element 548 of a screw 540. As shown in FIG. 5A, a second mating element 566 of a pressure cap 560 may comprise an external protrusion and may be inserted into a first mating element 548 comprising an internal recess such that the mobility of the screw head is restricted from polyaxial to monoaxial capabilities. As shown in FIG. 5B, a second mating element 566 of pressure cap 560 may comprise an internal recess and may receive a first mating element 548 comprising an external protrusion such that the mobility of the screw head is restricted from polyaxial to monoaxial capabilities.

In some embodiments a proximal end 562 of pressure cap 560 may comprise a surface configured to be compatible with a surface of a mounting rod 480 (e.g., FIG. 4A, 4B) (e.g., curved, partially curved, V-shaped). In some embodiments a mounting rod 480 (e.g., FIG. 4A, 4B) may be inserted into a mounting rod receiving channel 526 such that the mounting rod 480 (e.g., FIG. 4A, 4B) sits adjacent to a proximal end 522 of a pressure cap 560. Mounting rod 480 (e.g., FIG. 4A, 4B) may be secured against a proximal end 522 of pressure cap 560, in some embodiments, and may exert a bias and/or compression force upon pressure cap 560 via securing a compression element 992 (e.g., FIG. 9) at a proximal end of mounting rod receiving chamber 526 such that compression element is biased against mounting rod, as seen in FIG. 9.

Figure 6A:
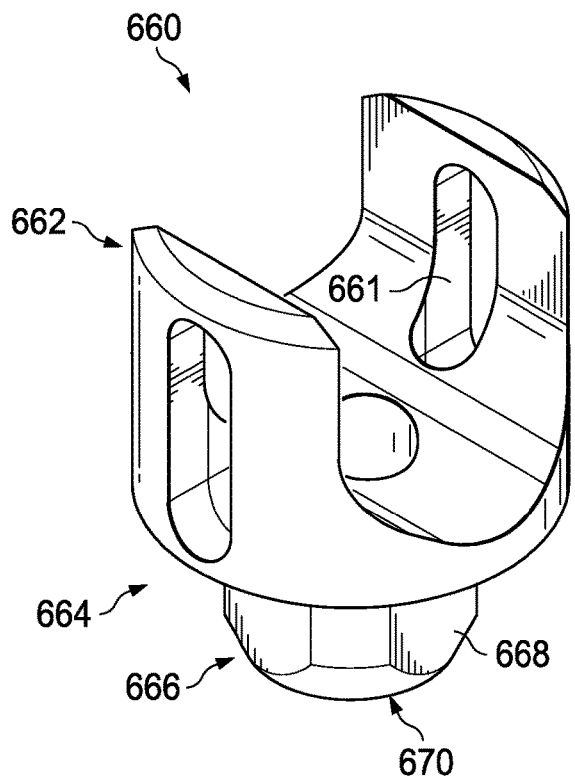
FIG. 6A illustrates a perspective view of a pressure cap according to an exemplary embodiment of the disclosure.
Figure 6B:
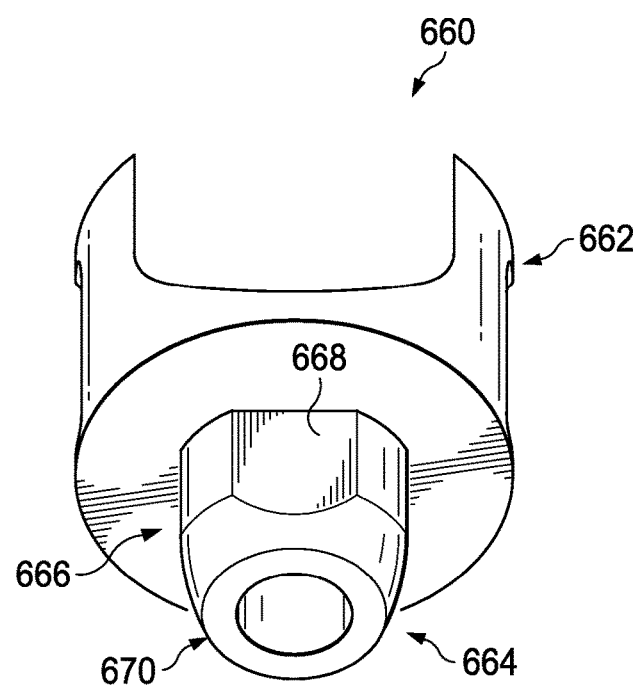
FIG. 6B illustrates a perspective view of a pressure cap according to an exemplary embodiment of the disclosure.
Figure 6C:
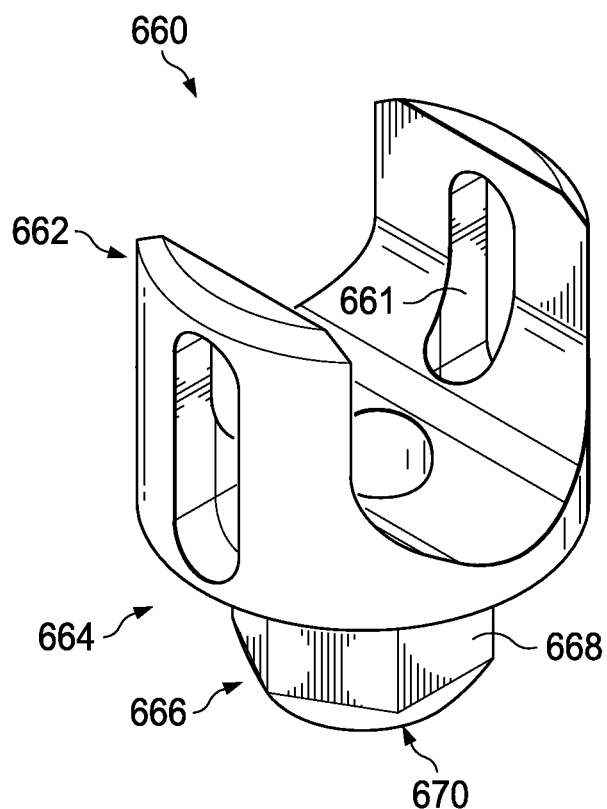
FIG. 6C illustrates a perspective view of a pressure cap according to an exemplary embodiment of the disclosure.
Figure 6D:
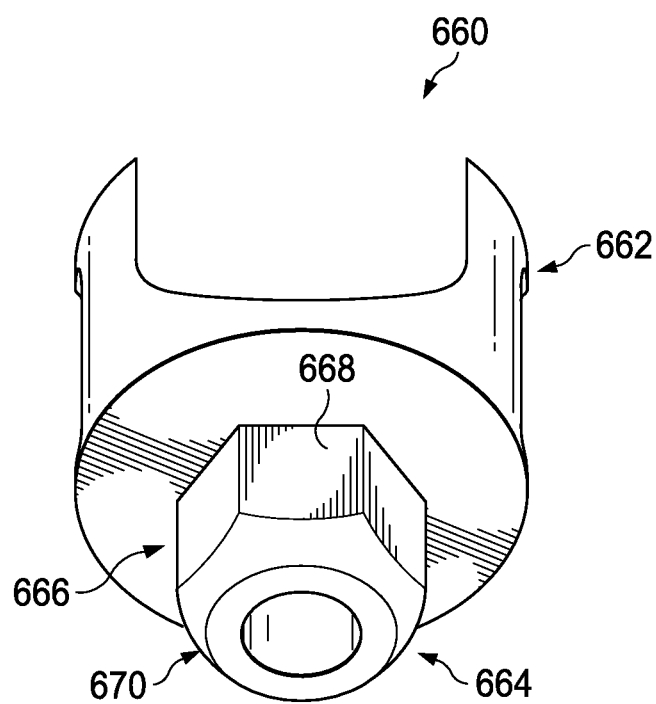
FIG. 6D illustrates a perspective view of a pressure cap according to an exemplary embodiment of the disclosure.
Figure 6E:
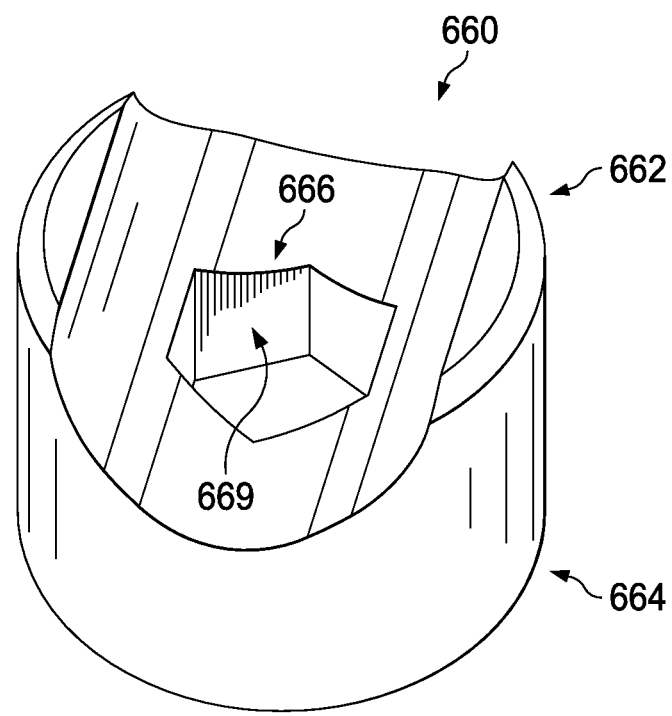
FIG. 6E illustrates a perspective view of a pressure cap according to an exemplary embodiment of the disclosure.

FIGS. 6A, 6B, 6C, 6D, and 6E illustrate perspective views of a pressure cap 660 according to exemplary embodiments of the disclosure. A pressure cap 660 may comprise a proximal end 662 and a distal end 664. A distal end 664 of pressure cap 660 may be inserted into a mounting rod receiving channel 526 (e.g., FIG. 5A) and travel from a proximal end 522 (e.g., FIG. 5A) of a body 520 (e.g., FIG. 5A) towards a distal end 524 of body 520. A second mating element 666 may be disposed on a distal end 664 of pressure cap 660. As shown in FIGS. 6A, 6B, 6C, and 6D, a second mating element 666 may comprise an external protrusion including a protrusion base 670 and a plurality of protrusion faces 668. As shown in FIG. 6E, a second mating element 666 may comprise an internal recess including a plurality of internal faces 669.

A second mating element 666 of a pressure cap 660 may be configured to mate with a first mating element 448 (e.g., FIG. 4A, 4B) of a screw 440 (e.g., FIG. 4A, 4B) such that the movement of screw 440 in a spinal fixation system may be restricted (e.g., to that of a mono-axial screw). In some embodiments, a second mating element 666 of a pressure cap 660 may have a size and/or shape corresponding with a first mating element 448 (e.g., FIG. 4A, 4B) of a screw head 446 (e.g., FIG. 4A, 4B). A second mating element 666 may comprise a width corresponding to a first mating element 448 (e.g., FIG. 4A, 4B) of a screw head 446 (e.g., FIG. 4A, 4B). In some embodiments, a second mating element 666 comprising an external protrusion, as shown in FIGS. 6A, 6B, 6C, and 6D, may comprise a length sufficient to allow first mating element 548 (e.g., FIG. 5A) to receive at least a portion of the second mating element 666. According to some embodiments, a second mating element 666 comprising an internal recess, as shown in FIG. 6E, may comprise a depth sufficient to receive at least a portion of a first mating element 548 (e.g., FIG. 5B).

According to some embodiments, a pressure cap 660 comprising a second mating element 666 of an external protrusion (e.g., FIG. 6A, 6B, 6C, 6D) may be a single structure. In other embodiments, a pressure cap 660 and a second mating element comprising an external protrusion may be separately manufactured and configured to be connectably modular. For example, a separate external protrusion may connectably attach to a distal end of a pressure cap via assembly (e.g., snap connection, screw/threading connection, engaging undercuts and flexible tab structures, epoxy).

Figure 8B:
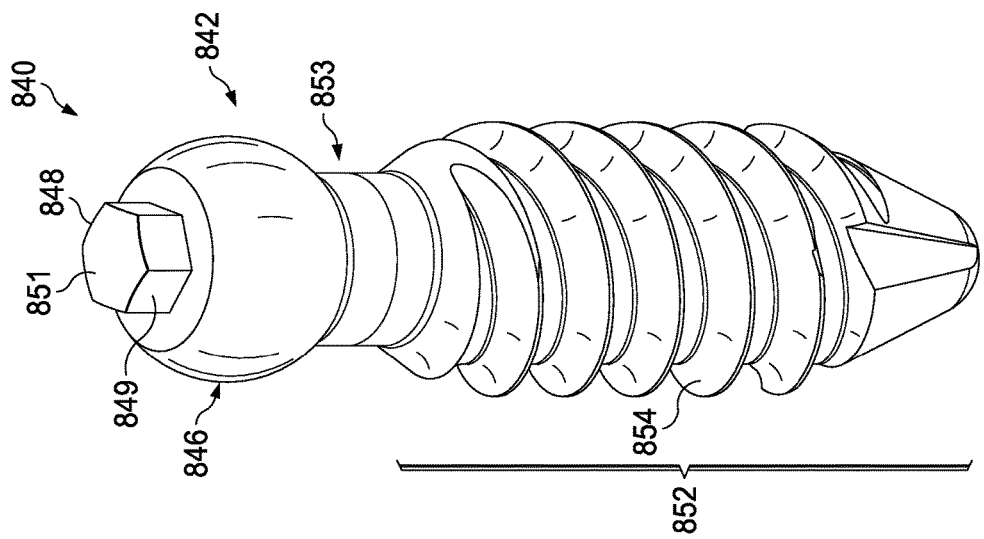
FIG. 8B illustrates a perspective view of screw according to an exemplary embodiment of the disclosure.
Figure 8A:
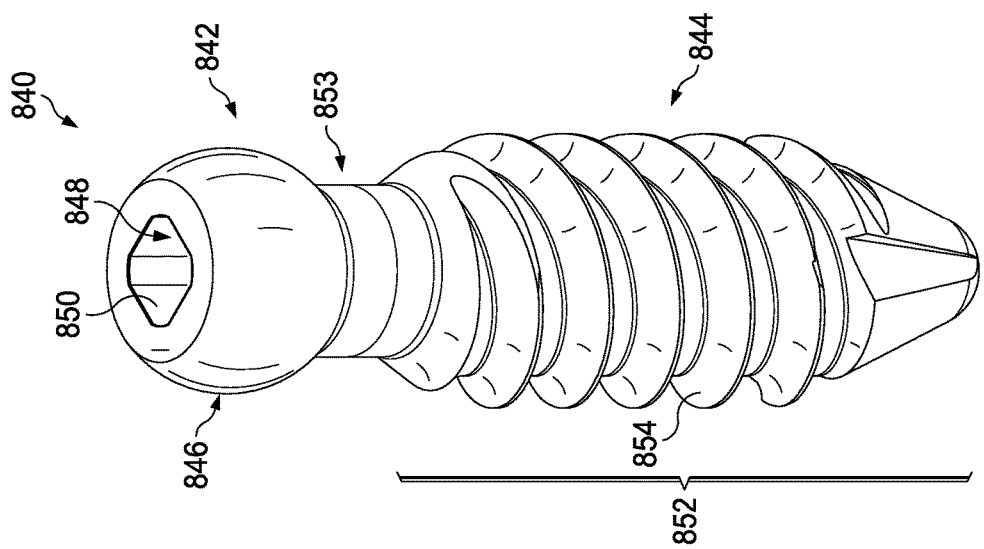
FIG. 8A illustrates a perspective view of screw according to an exemplary embodiment of the disclosure.

As shown in FIGS. 6A, 6B, 6C, and 6D a second mating element 666 may comprise an external protrusion that may be fitted into a first mating element comprising an internal recess such that a plurality of protrusion faces 668 of a second mating element may be substantially or completely aligned with a plurality of internal faces 850 (e.g., FIG. 8A) of the first mating element 848 (e.g., FIG. 8A). In some embodiments, a protrusion base 670 of a second mating element 666 may sit adjacent to or bias against a base of an internal recess 848 (e.g., FIG. 8A) of a first mating element. Such mating of protrusion faces 668 and/or a protrusion base 670 of a second mating element 660 with the shape of an internal recess of a first mating element 848 (e.g., FIG. 8A) may restrict the motion of a screw 240. More specifically, movement of a screw 240 (e.g., FIG. 2A) may be limited to that of a mono-axial screw. Described further, in some embodiments, if one attempts to rotate or pivot a screw 240 (e.g., FIG. 2A) within a body 220 (e.g., FIG. 2A), certain protrusion faces 668 (e.g., FIG. 6A, 6B, 6C, 6D) of an external protrusion of a second mating element 666 may be biased or pressured against a portion of an internal recess of a first mating element 848 (e.g., FIG. 8A). Likewise, in some embodiments, if one attempts to rotate or pivot screw 240 (e.g., FIG. 2A) within a body 220 (e.g., FIG. 2A), certain internal faces 669 (e.g., FIG. 6E) of an internal recess of a second mating element 666 (e.g., FIG. 6E) may be biased against protrusion faces 849 (e.g., FIG. 8B) of an external protrusion of a first mating element 848 (e.g., FIG. 8B). Accordingly, a second mating element 666 of a pressure cap 660 and a first mating element 848 of a screw head 846 may serve to constrain a screw 240 (e.g., FIG. 2A) to one position.

As shown in FIG. 6A and FIG. 6B, an external protrusion of a second mating element 666 may comprise a cube or right-rectangular prism segmented longitudinally by one or more arcs to form a protrusion base 670 and a plurality of protrusion faces 668. In other embodiments, an external protrusion of a second mating element 666 may comprise a cylinder segmented longitudinally by one or more arcs to form a protrusion base 670 and a plurality of protrusion faces 668. An external protrusion of second mating element 666 may be solid or hollow without departing from the description herein. Additional protrusions, cut-outs, moldings, or attachments may be present as part of an external protrusion to permit a more secure mating with an internal recess of a first mating element 848 (e.g., FIG. 8A) without departing from the current disclosure.

In other embodiments an external protrusion of second mating element 666 may have a plurality of protrusion faces 668 that may form protrusion base 670 with a polygonal shape. For example, as shown in FIG. 6C and FIG. 6D, an external protrusion of a second mating element 666 may have six protrusion faces 668, forming a protrusion base 670 in the shape of a hexagon. According to other embodiments of the present disclosure, the polygonal shape of protrusion base 670 may be a triangle, rectangle, pentagon, heptagon, octagon, or star-shaped. The number of protrusion faces 668 and the polygonal shape of protrusion base 670 may vary in different embodiments of the present disclosure without departing from the description herein.

Variations in the number of protrusion faces and the shape of a protrusion base 670 may provide for various advantages. For example, an external protrusion of a second mating element 666 with more protrusion faces or protrusion faces that provide increased surface area may decrease the amount of friction created when protrusion faces 668 interact with internal faces 850 (e.g., FIG. 8A) of an internal recess of a first mating element 848 (e.g., FIG. 8A). As another example, an external protrusion 666 with fewer protrusion faces 668 may be easier to manufacture.

Dimensions of an external protrusion 666, along with protrusion faces 668 and protrusion base 670 may vary in different embodiments of the present disclosure without departing from the description herein. According to some embodiments of the present disclosure, an external protrusion of second mating element 666 may have a height of about 2 mm to about 5 mm. According to some embodiments of the present disclosure, external protrusion of second mating element 666 may have a width of about 2.5 mm to about 5 mm.

Variations in the dimensions of external protrusion of second mating element 666 may provide for various advantages. For example, a greater height of external protrusion of second mating element 666 or protrusion faces 668 may allow for a better mating of second mating element 666 of pressure cap 660 with an internal recess of first mating element 848 (e.g., FIG. 8A) of screw 840 (e.g., FIG. 8A). As another example, a greater or lesser width of an external protrusion of a second mating element 666 may allow for a more convenient design of an internal recess of a first mating element 848 (e.g., FIG. 8A), or a more secured mating of a second mating element 666 with a first mating element 848 (e.g., FIG. 8A). As yet another example, particular dimensions for an external protrusion 666 may be more advantageous depending on the intended anatomical location of the spinal fixation system.

As shown in FIGS. 6A and 6C, a pressure cap 660 may further comprise two pressure cap pin holes 661 disposed across from one another on opposing walls of pressure cap 660. In some embodiments, when a pressure cap is fixed within a body 920 (e.g., FIG. 9) in a position adjacent to a screw 940 (e.g., FIG. 9) body pin holes 921 and pressure cap holes 661, 961 align such that holding pin 994 may be received there through. One holding pin 994 (e.g., FIG. 9) may be disposed within each of the two aligned body pin holes 921 and pressure cap pin holes 661, 961.

Figure 7:
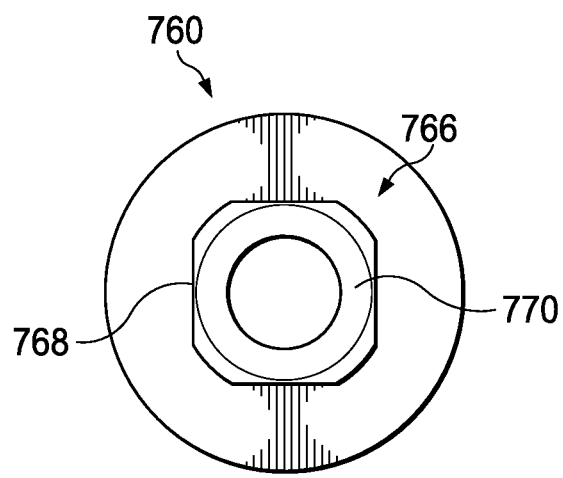
FIG. 7 illustrates a bottom-up view of an external protrusion of a pressure cap according to an exemplary embodiment of the disclosure.

FIG. 7 illustrates a bottom-up view of a second mating element 766 comprising an external protrusion of pressure cap 760 according to an exemplary embodiment of the disclosure. As shown in FIG. 7, a pressure cap 760 may comprise a second mating element comprising an external protrusion 766 with a plurality of protrusion faces 768 and a protrusion base 770.

FIGS. 8A and 8B illustrate perspective views of screws according to certain embodiments of the disclosure. A screw 840 comprises a proximal end 842 and a distal end 844. A head 846 of screw 840 may be disposed at proximal end 842. A bone connection element 852 may be disposed towards distal end 844 of screw 840. In some embodiments, a screw 840 may further comprise an intermediate region 853 disposed between head 846 and connection element 852.

A head 846 of screw 840 may have a substantially spherical surface. In some embodiments, a head 846 of screw 840 may be entirely spherical but for a proximate portion to accommodate a first mating element 848 and a distal portion to accommodate an intermediate region 853 or a bone connection element 852. A radius of the spherical surface of head 846 may vary in different embodiments of the present disclosure without departing from the description herein. According to some embodiments, a radius of a spherical surface of head 846 may be about 3.5 mm to about 12 mm. Screws 840 with different sized heads 846, as defined by the radius of spherical surfaces, may be more appropriate in different circumstances. For example, a screw 840 used for the cervical and upper thoracic regions may have a smaller head 846 or a smaller radius for the spherical surface of head 846. As another example, a screw 840 used for the lumbar or lower thoracic regions may have a larger head 846 or a larger radius for the spherical surface of head 846.

A bone connection element 852 of screw 840 may comprise an external thread 854. An external thread 854 may allow a screw 840 to be secured into a bone. In some embodiments, an external thread 840 may be secured into a portion of a spine (e.g., pedicle region, iliac region, cervical region). The dimensions of a bone connection element 852 along with the pattern and structure of an external thread 854 may be varied to achieve different effects without departing from the description herein. For example, screws 840 with different lengths or diameters may be more appropriate for different regions of a spine. According to some embodiments of the present disclosure, the spinal fixation system may be secured to a cervical and upper thoracic region. In such embodiments, the major diameter of a bone connection element 852 may range from about 2.5 mm to about 5 mm, and the length of the bone connection element 852 may range from about 6 mm to about 50 mm. According to some embodiments of the present disclosure, the spinal fixation system may be secured to a lumbar or a lower thoracic region. In such embodiments, the major diameter of a bone connection element 852 may range from about 4 mm to about 12 mm, and the length of a bone connection element 852 may range from about 20 mm to about 120 mm.

As shown in FIG. 8A and FIG. 8B, a first mating element 848 may be disposed on a screw head 846. In some embodiments, a first mating element 848 may comprise an internal recess, as shown in FIG. 8A. A first mating element 848 comprising an internal recess may comprise a plurality of internal faces 850 configured to mate with an external protrusion of a second mating element 666 (e.g., FIG. 6A), in some embodiments. As shown in FIG. 8B, a first mating element 848 may comprise an external protrusion including a protrusion base 851 and a plurality of protrusion faces 849. According to some embodiments, a screw 840 comprising a first mating element 848 of an external protrusion may be a single structure. In other embodiments, a screw 840 and a first mating element 848 comprising an external protrusion may be separately manufactured and configured to be connectably modular. For example, a separate external protrusion may connectably attach to a screw head 846 of a screw 840 via assembly (e.g., snap connection, screw/threading connection, engaging undercuts and flexible tab structures, epoxy).

A first mating element 848 of a screw 840 may be configured to mate with a second mating element 466 (e.g., FIG. 4A, FIG. 4B) of pressure cap (e.g., FIG. 6A, 6B, 6C, 6D, 6E) such that movement of screw 840 in the spinal fixation system may be restricted (e.g., to that of a monoaxial screw). In some embodiments, a first mating element 848 of a screw 840 may have a size and/or shape corresponding with a second mating element 466 (e.g., FIG. 4A, FIG. 4B) of a pressure cap 460 (e.g., FIG. 4A, FIG. 4B).

First mating element 848 may comprise a width corresponding to second mating element 466 (e.g., FIG. 4A, FIG. 4B). According to some embodiments, a first mating element 848 comprising an internal recess, as shown in FIG. 8A, may comprise a depth sufficient to receive at least a portion of a second mating element 566 (e.g., FIG. 5B). In some embodiments, a first mating element 848 comprising an external protrusion, as shown in FIG. 8B, may comprise a length sufficient to allow second mating element 566 (e.g., FIG. 5A) to receive at least a portion of the first mating element 848.

As shown in FIG. 8B, an external protrusion of a first mating element 848 may have a plurality of protrusion faces 849 that may form a protrusion base 851 with a polygonal shape. For example, as shown in FIG. 8B, an external protrusion of a first mating element 848 may have six protrusion faces 849, forming protrusion base 851 in the shape of a hexagon. According to other embodiments of the present disclosure, the polygonal shape of protrusion base 851 may be a triangle, rectangle, pentagon, heptagon, octagon, or star-shaped. The number of protrusion faces 849 and the polygonal shape of protrusion base 851 may vary in different embodiments of the present disclosure without departing from the description herein.

In some embodiments a first mating element comprising an external protrusion may comprise a cube or right-rectangular prism segmented longitudinally by one or more arcs to form protrusion base 851 and protrusion faces 849. In other embodiments, external protrusion of a first mating element 848 may comprise a cylinder segmented longitudinally by one or more arcs to form a protrusion base 851 and a plurality of protrusion faces 849. An external protrusion of a first mating element 848 may be solid or hollow without departing from the description herein. Additional protrusions, cut-outs, moldings, or attachments may be present as part of the external protrusion to permit a more secure mating with internal recess of second mating element without departing from the current disclosure.

Variations in the number of protrusion faces and the shape of protrusion base 670 may provide for various advantages such as increased surface area or ease of manufacturing.

Dimensions of external protrusion of a first mating element 848, along with a plurality of protrusion faces 849 and a protrusion base 851 may vary in different embodiments of the present disclosure without departing from the description herein. According to some embodiments of the present disclosure, an external protrusion of a first mating element 848 may have a height of about 2 mm to about 5 mm. According to some embodiments of the present disclosure, an external protrusion of first mating element 848 may have a width of about 2.5 mm to about 5 mm.

Variations in the dimensions of external protrusion of a first mating element 848 may provide for various advantages. For example, a greater height of an external protrusion of a first mating element 848 or a plurality of protrusion faces 849 may allow for a better mating of a first mating element 848 of screw 840 with an internal recess of a second mating element 666 (e.g., FIG. 6E) of pressure cap 660 (e.g., FIG. 6E). As another example, a greater or lesser width of external protrusion of first mating element 848 may allow for a more convenient design of internal recess of second mating element 666 (e.g., FIG. 6E), or a more secured mating of second mating element 666 with first mating element 848. As yet another example, particular dimensions for external protrusion of first mating element 848 may be more advantageous depending on the intended anatomical location of the spinal fixation system.

FIG. 9 illustrates a profile view of a mounting rod 980, a pressure cap 960, a body 920, and a pedicle screw 940 fitted together according to a specific example embodiment of the disclosure. As seen in FIG. 9, a spinal fixation system may comprise a screw 940 that may be engaged with a body 920 by being received in a screw head receiving aperture 130 (e.g., FIG. 1). Screw 940 may comprise a bone connection element 852 (FIG. 8A) with external thread 854 (FIG. 8A) operable for being fastened or screwed into a bone. Screw 940 may further comprise screw head 946 and a first mating element 948 disposed on screw head 946.

A pressure cap 960 may be inserted into body 920 and sit adjacent to screw head 946. A second mating element 966 of pressure cap 960 may mate with first mating element 948 of screw head 946. In some embodiments, pressure cap 960 may further comprise two pressure cap pin holes 961 disposed across from one another on opposing walls of pressure cap 960. Pressure cap 960 may be secured within body 920 in a position adjacent to and/or biased against screw 940 by the insertion of holding pin 994 through body pin hole 921 and pressure cap pin hole 961. A holding pin 994 may be disposed within each of the two aligned body pin holes 921 and pressure cap pin holes 961.

As shown in FIG. 9, mounting rod 980 may be disposed or placed into the body through mounting rod receiving channel 926. Mounting rod 980 may be disposed in such a manner such that a proximal portion of body 920 comprising an internal thread 918 may be exposed and may be operable to receive a compression element 992. Compression element 992 may comprise external threads which complement internal threading 918 of body 920. In some embodiments, a compression element 992 may be secured such that the compression element exerts a compressive force against mounting rod 980. The compressive force on mounting rod 980 allows mounting rod 980 to bias against or be pressed down on pressure cap 960. The resulting compressive forces may promote a more secure and stable assembly or spinal fixation system.

In any of the embodiments of the present disclosure, the materials may be chosen and may be varied to fit a number of functional and design considerations. In some embodiments, screw 140, 240, 440, 540, 840, 940; tower 102, 302; body 120, 220, 320, 420, 520, 920; attachment portion 104, 304; pressure cap 260, 360, 460, 560, 660, 760, 960; mounting rod 480, 980; and compression element 992 may be made of materials such as titanium, titanium alloy, stainless steel, cobalt chrome, PEEK, carbon fiber, nitinol, Mo—Re, or any combination thereof. However, any implantable or biocompatible material may be used without departing from the description herein. Furthermore, a material for each component may be independently selected and a material of each component may vary from one another without departing from the description herein.

The present disclosure relates, in some embodiments, to methods of affixing a spinal fixation system to a bone. The method may comprise engaging a screw 440 with a body 420. Screw 440 may comprise head 446 at proximal end 142, bone connection element 452 towards distal end 144, and internal recess 448 disposed on the head 446 of the screw 440. Body 420 may comprise proximal end 422, distal end 424, mounting rod receiving channel 326 (e.g., FIG. 3) disposed at proximal end 422 of body 420, and screw head receiving aperture 430 disposed at distal end 424 of body 420. Proximal end 422 and distal end 424 may be disposed along a longitudinal axis.

To engage with body 420, body 420 may be lowered onto screw 440 such that screw head 446 fits securely within screw head receiving aperture 430.

The method may further comprise securing a bone connection element 452 of a screw 440 into a bone. The securing of the screw may be done through a number of mechanical means. Bone connection element 452 may be secured to a bone either before or after engagement of screw head 446 with body 420.

In some embodiments body 420 comprises a portion of tower 102 (e.g., FIG. 1). Tower 102 may comprise body 120, 420 and an attachment portion 104 (FIG. 1).

In some embodiments, the method may further comprise selecting a pressure cap. Pressure cap 460 may be received within body 420. Pressure cap 460 may comprise proximal end 462, distal end 464, and second mating element 466 disposed on the distal end 464 of pressure cap 460. A second mating element 466 may be configured to mate with a first mating element 448 of screw 440 so as to limit the movement of screw 440.

In some embodiments, a method may comprise assembling a modular pressure cap 460 or a modular screw 440. In some embodiments, assembly of a modular pressure cap 460 or a modular screw 440 may comprise connectably attaching a separate external protrusion a screw head 446 or a distal end 664 (e.g., FIG. 6A) of pressure cap 460 snap connection, screw/threading connection, engaging undercuts and flexible tab structures, epoxy, or any combination thereof.

The method may further comprise mating second mating element of pressure cap 460 with first mating element 448 of screw head 446. Pressure cap 460 may be fitted on or fitted against head 446 of screw 440 within body 420. The mating of second mating element 466 and first mating element 448 may serve to limit the movement of screw 440.

In some embodiments, the method may further comprise fitting a mounting rod 480 within the mounting rod receiving channel 326 (e.g., FIG. 3) of body 420. Mounting rod 480 may be disposed against proximate end 462 of pressure cap 460.

The method may further comprise securing a compression element 992 within mounting rod receiving channel 326 (e.g., FIG. 3). The securing of the compression element may create a compressive force on mounting rod 480 that may allow mounting rod 480 to bias against or be pressed down on pressure cap 460. The resulting compressive forces may promote a more secure and stable assembly or spinal fixation system.

According to some embodiments, a method may comprise engaging a screw 440 with a body 420. Screw 440 may comprise head 446 at proximal end 142, bone connection element 452 towards distal end 144, and intermediate region 253 disposed between head 446 and bone connection element 452. Body 420 may comprise proximal end 422, distal end 424, mounting rod receiving channel 326 (e.g., FIG. 3) disposed at proximal end 422 of body 420, and screw head receiving aperture 430 disposed at distal end 424 of body 420. Proximal end 422 and distal end 424 may be disposed along a longitudinal axis.

To engage with body 420, body 420 may be lowered onto screw 440 such that screw head 446 fits securely within screw head receiving aperture 430.

According to some embodiments, the method may further comprise rotatably connecting a blocking ring 296 to screw 440, body, 420, or both. In some embodiments, rotatably connecting a blocking ring 296 to a screw 440, a body, 420, or both may include a snap connection, a screw/threading connection, engagement of undercuts and flexible tab structures, or any combination thereof. Blocking ring 296 may comprise a proximal surface 297 and a distal surface 298. According to some embodiments, blocking ring 296 may further comprise at least one slot 299 extending between a distal surface 298 and a proximal surface 297. The at least one slot 299 may be configured to confine the screw 440 to restricted planes or a single plane of pivotal movement. Blocking ring, in some embodiments, may comprise one or more indentations 295 in a proximal surface 297, a distal surface 298, on an underside, or any combination thereof. The one or more indentations may be configured to confine a screw 440 to restricted planes or a single plane of pivotal movement.

The method may further comprise securing a bone connection element 452 of a screw 440 into a bone. The securing of the screw 440 may be done through a number of mechanical means. Bone connection element 452 may be secured to a bone either before or after engagement of screw head 446 with body 420.

According to some embodiments, the method may further comprise rotating a blocking ring 296 to align slot 299 with a desired plane in which screw 440 may pivot (e.g., FIG. 2B).

In some embodiments body 420 comprises a portion of tower 102 (e.g., FIG. 1). Tower 102 may comprise body 120, 420 and an attachment portion 104 (FIG. 1).

In some embodiments, the method may further comprise selecting a pressure cap. Pressure cap 460 may be received within body 420. Pressure cap 460 may comprise proximal end 462 and a distal end 464. The method may further comprise fitting pressure cap 460 on or against head 446 of screw 440 within body 420.

In some embodiments, the method may further comprise fitting a mounting rod 480 within the mounting rod receiving channel 326 (e.g., FIG. 3) of body 420. Mounting rod 480 may be disposed against proximate end 462 of pressure cap 460.

The method may further comprise securing a compression element 992 within mounting rod receiving channel 326 (e.g., FIG. 3). The securing of the compression element may create a compressive force on mounting rod 480 that may allow mounting rod 480 to bias against or be pressed down on pressure cap 460. The resulting compressive forces may promote a more secure and stable assembly or spinal fixation system.

Any of the features, variations, and other embodiments described above for the articles and systems of the present disclosure may apply to the presently disclosed methods without departing from there description herein.

As will be understood by those skilled in the art who have the benefit of the instant disclosure, other equivalent or alternative compositions, devices, methods, and systems for a convertible screw can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/− about 10%, depicted value +/− about 50%, depicted value +/− about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for a spinal fixation system may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

What is claimed is:

1. A spinal fixation system, comprising:
   a screw comprising:
      a screw head at a proximal end;
      a bone connection element at a distal end; and
      a first mating element disposed on the screw head;
      wherein the first mating element is an internal recess;
   a body comprising:
      a proximal end relative to a longitudinal axis of the body;
      a distal end relative to the longitudinal axis;
      a mounting rod receiving channel disposed at the proximal end and configured to receive a mounting rod; and
      a screw head receiving aperture disposed at the distal end of the body, wherein the screw head receiving aperture is configured to permit poly-axial movement of the screw head within the screw head receiving aperture; and
   a pressure cap configured to be disposed within the body between the mounting rod and the screw comprising:
      a proximal end relative to a longitudinal axis of the pressure cap;
      a distal end relative to the longitudinal axis of the pressure cap; and
      a second mating element disposed on the distal end of the pressure cap;
      wherein the second mating element is an external protrusion;
   wherein the internal recess of the screw is configured to mate with the external protrusion of the pressure cap thereby limiting the pivotal movement of the screw to that of a monoaxial screw.

2. The spinal fixation system of claim 1, wherein the pressure cap is manufactured as a single piece comprising an external protrusion.

3. The spinal fixation system of claim 1, wherein the second mating element is connectably attached to the pressure cap.

4. The spinal fixation system of claim 1,
   wherein the external protrusion comprises a protrusion base and a plurality of protrusion faces;
   wherein the internal recess comprises a plurality of internal faces;
   wherein the plurality of protrusion faces are configured to mate with the plurality of internal faces.

5. The spinal fixation system of claim 4, wherein the plurality of protrusion faces form a protrusion base with a polygonal shape.

6. The spinal fixation system of claim 5, wherein the polygonal shape is selected from the group consisting of a triangle, rectangle, pentagon, hexagon, heptagon, octagon, or star.

7. The spinal fixation system of claim 4, wherein the external protrusion comprises a cube or right-rectangular prism segmented longitudinally by one or more arcs to form the protrusion base and the plurality of protrusion faces.

8. The spinal fixation system of claim 4, wherein the external protrusion comprises a cylinder segmented longitudinally by one or more arcs to form the protrusion base and the plurality of protrusion faces.

9. The spinal fixation system of claim 1, wherein the screw is selected from a pedicle screw, an iliac screw, and a cervical screw.

10. The spinal fixation system of claim 1, wherein the body is frangibly connected to an attachment portion to form a tower.

11. A spinal fixation system, comprising:
    a body comprising:
       a proximal end relative to a longitudinal axis of the body;
       a distal end relative to the longitudinal axis;

a mounting rod receiving channel disposed at the proximal end of the body and operable to receive a mounting rod; and a screw head receiving aperture disposed at the distal end of the body, wherein the screw head receiving aperture is operable to permit poly-axial movement of a screw head within the screw head receiving aperture; and a pressure cap operable to be disposed within the body between the mounting rod and a screw, the pressure cap comprising:

a proximal end relative to a longitudinal axis of the pressure cap;

a distal end relative to the longitudinal axis of the pressure cap; and an external protrusion disposed on the distal end of the pressure cap;

wherein the external protrusion of the pressure cap is operable to mate with an internal recess disposed on the head of the screw, thereby limiting pivotable movement of the screw.

12. A method of affixing a spinal fixation system, the method comprising:

engaging a screw within a body;
wherein the screw comprises:
a head at a proximal end;
a bone connection element at a distal end; and
an internal recess disposed on the head of the screw; and wherein the body comprises:
a proximal end relative to a longitudinal axis of the body;
a distal end relative to the longitudinal axis;
a mounting rod receiving channel disposed at the proximal end; and
a screw head receiving aperture disposed at the distal end of the body, wherein the screw head receiving aperture securely receives the screw head;

securing the bone connection element in a bone;
selecting a pressure cap,
wherein the pressure cap comprises:
a proximal end relative to a longitudinal axis of the pressure cap;
a distal end relative to the longitudinal axis of the pressure cap;
an external protrusion disposed on the distal end of the pressure cap; and wherein the internal recess of the screw is configured to mate with the external protrusion of the pressure cap thereby limiting the pivotal movement of the screw to that of a monoaxial screw;

mating the internal recess of the screw with the external protrusion of the pressure cap;

fitting a mounting rod within the mounting rod receiving channel so that the rod is disposed against the proximate end of the pressure cap; and securing the compression element within the mounting rod receiving channel so that a bias is applied by the mounting rod against the pressure cap.

13. A method of affixing a spinal fixation system, the method comprising:

fitting a screw within a tower;
wherein the screw comprises:
a head at a proximal end;
a bone connection element at a distal end; and
an internal recess disposed on the head of the pedicle screw; and wherein the tower comprises a body and an attachment portion, wherein the body comprises:
a proximal end relative to a longitudinal axis of the body;
a distal end relative to the longitudinal axis;
a mounting rod receiving channel disposed at the proximal end; and
a screw head receiving aperture disposed at the distal end of the body, wherein the screw head receiving aperture securely receives the screw head;

securing the bone connection element in a bone,
selecting a pressure cap,
wherein the pressure cap comprises:
a proximal end relative to a longitudinal axis of the pressure cap;
a distal end relative to the longitudinal axis of the pressure cap;
an external protrusion disposed on the distal end of the pressure cap; and wherein the internal recess of the screw is configured to mate with the external protrusion of the pressure cap thereby limiting the pivotal movement of the screw to that of a monoaxial screw;

mating the external protrusion of the pressure cap with the internal recess of the screw head;

fitting a mounting rod within the mounting rod receiving channel so that the rod is disposed against the proximate end of the pressure cap; and securing the compression element within the mounting rod receiving channel so that a bias is applied by the mounting rod against the pressure cap.

* * * * *